United States Patent [19]

Kojima et al.

[11] 4,189,321

[45] Feb. 19, 1980

[54] PROCESS FOR FORMING MAGENTA DYE IMAGES

[75] Inventors: Tamotsu Kojima; Mitsuto Fujiwhara; Takaya Endo; Osamu Ezawa, all of Hino, Japan

[73] Assignee: Konishiroku Photo Industry Co., Ltd., Tokyo, Japan

[21] Appl. No.: 936,915

[22] Filed: Aug. 24, 1978

[30] Foreign Application Priority Data

Aug. 31, 1977 [JP] Japan .................................. 52-104437

[51] Int. Cl.$^2$ ............................................... G03C 7/00
[52] U.S. Cl. ..................................... 430/381; 430/386
[58] Field of Search ........................... 96/100, 56.5, 56

[56] References Cited

U.S. PATENT DOCUMENTS

| 2,294,909 | 9/1942 | Jennings | 96/100 |
| 2,618,641 | 11/1952 | Weissberger et al. | 96/100 |
| 3,861,923 | 1/1975 | Hara et al. | 96/56 |
| 3,909,267 | 9/1975 | Iwano et al. | 96/56 |
| 3,926,634 | 12/1975 | Sugizaki et al. | 96/100 |

*Primary Examiner*—J. Travis Brown
*Attorney, Agent, or Firm*—Haseltine, Lake & Waters

[57] ABSTRACT

A process for forming color photographic images using magenta couplers which afford excellent resistance to formalin, is described.

11 Claims, No Drawings

PROCESS FOR FORMING MAGENTA DYE IMAGES

This invention relates to a process for forming color photographic images and particularly is concerned with a process for forming color photographic images using novel magenta couplers excellent in property resisting to formalin.

In the field of photographic art for photoinformation recording purposes, silver halides are being widely used because of their excellent photographic characteristics such as sensitivity, gradation, etc. In the case where such silver halide is used as a photosensitive component in a light-sensitive photographic material in order to eventually obtain a dye image thereon, generally the silver halide is used in combination with a certain kind of color forming compound, whereby a desired dye image is obtained by reacting this color forming compound with a certain kind of reactive compound while forming the dye correspondingly to an imformation recorded on said silver halide. This color forming compound is a coupler and the reactive compound used in combination with the coupler is generally a color developing agent, for example, an aromatic primary amine type developing agent such as p-phenylenediamine developing agent.

Light-sensitive photographic materials usually include those of an outer type which are processed with color developers containing diffusible couplers on one hand and those of an inner type on the other hand, wherein dispersions of non-diffusible couplers are individually incorporated beforehand into light-sensitive layers so that said couplers may retain their respective independent functions in the respective layers where they are present until the photographic materials are processed with color developers. In the case of the photographic materials of an inner type, usually a yellow coupler for forming a yellow dye is incorporated into a blue-sensitive layer, a magenta coupler for forming a magenta dye into a green-sensitive layer, and a cyan coupler for forming a cyan dye into a red-sensitive layer, and when the photographic materials are developed after light-exposure in the presence of an aromatic primary amine type color developing agent, the color developing agent reduces the silver halide to a developed silver and at the same time the color developing agent, per se, is oxidized to an active oxidation product of said color developing agent. This oxidation product and each of the couplers present in the light-sensitive layers undergo coupling reaction to form a colored dye, with the result that the respective dye images are formed correspondingly to the information recorded on individual light-sensitive layer.

Under such circumstances, various magenta couplers which are 5-pyrazolone derivatives are used in order to form magenta dye images. The reaction of said 5-pyrazolone type magenta coupler with an oxidation product of a color developing agent is brought about at an active point of said coupler, and said active point is present in an active methylene group (at the 4-position of 5-pyrazolone) in the molecule of said 5-pyrazolone type magenta coupler.

Magenta couplers having at the active point such groups, i.e. so-called split-off groups, as capable of being released at the time of reaction of said coupler with an oxidation product of a color developing agent are called active point-substituted type magenta couplers.

Active point-substituted type magenta couplers heretofore known include, for example, those of halogen-substituted type (U.S. Pat. No. 3,006,579, etc.), of aryloxy-substituted type (U.S. Pat. No. 3,419,391, etc.), of carbonyloxy-substituted type (U.S. Pat. Nos. 3,311,476 and 3,432,521, Japanese Laid-Open-to-Public Publn. No. 129538/1974, etc.), of nitrogen- or sulfur-substituted type (Japanese Laid-Open-to-Public Publn. Nos. 53435/1974, 53436/1974, 53372/1975, 122935/1975, etc.), of carbon-substituted type (U.S. Pat. No. 2,632,702, Japanese Laid-Open-to-Public Publn. No. 37646/1976, etc.), of substituted methylene-substituted type (British Patent No. 968,461, Japanese Patent Publn. No. 4086/1959, etc.), and of methylene, alkylidene or arylidene bis type (U.S. Pat. No. 2,618,864, British Pat. Nos. 786,859 and 968,461, Japanese Patent Publn. Nos. 16110/1969, 26589/1969 and 37854/1974, Japanese Laid-Open-to-Public Publn. No. 29638/1974, etc.). These magenta couplers of the types mentioned above have such characteristic features as high dye forming speed, high maximum color density and the like, but on the other hand they have certain drawbacks common to all. That is, these known active point-substituted type magenta couplers have such drawbacks that because of their instability, they are less stable when present in the coated emulsion layers, liable to undesirable interactions with other photographic additives coexisting therewith, and bring about the drop in color forming speed or maximum density and the formation of fog. As is clear from the working examples set forth later on, the greatest defect associated with these known magenta couplers of the type is that said couplers are very poor in property resisting to formalin gas. That is, formalin reacts with the active point of magenta coupler, whereby the magenta coupler is markedly lowered in color forming property at the time when color development is carried out.

Accordingly, it is an object of the present invention to provide novel active point-substituted type magenta couplers which are quite excellent in property resisting to formalin gas and which give magenta dye images excellent in graininess and, at the same time, provide a process for forming magenta dye images by color development of a light-sensitive silver halide photographic material using said magenta couplers.

Other objects of the present invention will become apparent from the description and working examples which follow.

Extensive studies and investigations conducted by us have resulted in the finding that the above-mentioned objects of the present invention can be accomplished by virtue of magenta couplers which are obtained by reacting at least one 5-pyrazolone compound with a compound having two or more aldehydo groups, said couplers having in the molecule at least four residues the 5-pyrazolone compounds, from each of which one hydrogen atom at the 4-position has been removed.

The 5-pyrazolone compounds used in the present invention include compounds represented by the following general formula [I].

General formula [I].

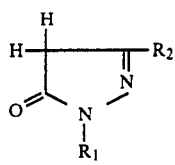

wherein $R_1$ and $R_2$ individually represent such groups as may be used in common 4-equivalent type 5-pyrazolone couplers. More concretely, the definition of $R_1$ includes a hydrogen atom, an alkyl group (e.g. methyl, ethyl, isopropyl, t-butyl, n-hexyl, t-octyl, dodecyl, heptaphloropropyl, hexaphloropropyl, etc.), an alkenyl group (e.g. allyl etc.), a cycloalkyl group (e.g. cyclohexyl etc.), a terphenyl group (e.g. norbonyl, etc,), an aryl group (e.g. phenyl and naphthyl, etc.), and a heterocyclic group (e.g. pyridyl, quinolyl, furyl, benzothiazolyl, oxazolyl, imidazolyl, naphthoxazolyl, etc.) and further includes the above-mentioned groups having individually introduced therein such substituent, for example, as a halogen atom, nitro, cyano, amino, alkyl, aralkyl, alkenyl, aryl, alkoxy, hydroxy, aryloxy, ester, carbonyl, sulfamoyl, carbamoyl, ureido, heterocycle, sulfonyloxy, oxo, acylamino, carboxyl, sulfonamido, alkylthio or arylthio, and these substituted groups, of which the substituents have been further substituted by such groups as mentioned above. Of the groups for $R_1$, a phenyl group, of which at least one of the ortho-position has been substituted, for example, by an alkyl group, an alkoxy group or a halogen atom, is particularly useful.

$R_2$ includes, in addition to such groups for the aforesaid $R_1$ as a hydrogen atom, an alkyl, aryl and heterocyclic group, an ester group (e.g. methyl ester, ethyl ester, phenyl ester, benzyl ester, etc.), an oxy group such as alkoxy, aryloxy, heterocyloxy, etc. (e.g. methoxy, ethoxy, phenoxy, tolyloxy, pyridyloxy, etc.), a thio group such as alkylthio, arylthio, etc. (e.g. ethylthio, propylthio, phenylthio, tolylthio, etc.), a carboxy group, an amino group such as amino, alkylamino, arylamino, heterocyclic amino, etc. (e.g. alkylamino, cycloalkylamino, N,N-dialkylamino, N-alkyl-N-allylamino, N-arylamino, pyridylamino, etc.), an acylamino group (e.g. N-alkylacylamino, N-arylacylamino, etc.), an ureido group (e.g. N-arylureido, N-alkylureido, etc.), a thioureido group (e.g. N-alkylthioureido, N-arylthioureido, etc.), a carbamoyl group (e.g. N-octadecylcarbamoyl, 3-pentadecylphenyl-carbamoyl, etc.), a thiocarbamoyl group, a guanidino group (e.g. guanidino, N-alkylguanidino, N-arylguanidino, etc.), and a sulfamoyl group.

The compound having aldehydo groups used in the present invention includes compounds represented by the following general formula [II].

General formula [II]

wherein n represents an integer of 2 or more, and when n is 2, Z represents a single bond or a divalent organic group, and when n is 3 or more, Z represents an n-valent organic group. More particularly, the n-valent organic group includes n-valent aliphatic hydrocarbon residues such as an alkylene group (e.g. methylene, ethylene, 1,2-propylene, 1,3-propylene, 1,4-butylene, 1,5-pentylene, 1,6-hexylene, 1,9-octylene, etc.), an alkenylene group (e.g. vinylene, propenylene, butenylene, etc.), an alkynylene group (e.g. ethynylene, etc.), a cycloalkylene group (e.g. 1,3-cyclopentylene, 1,4-cyclohexylene, etc.), an alkanetriyl group (e.g. 1,2,3-cyclohexylene, etc.), an alkanetriyl group (e.g. 1,2,3-propanetriyl, 1,2,4-butanetriyl, etc.) and an alkanetetrayl group (e.g. 1,3,5,7-heptanetetrayl, etc.), an arylene group (e.g. 1,3-phenylene, 1,4-phenylene, 1,3-naphthylene, etc.), an n-valent aromatic hydrocarbon residue such as a trivalent aromatic hydrocarbon (e.g. 1,3,5-benzenetriyl, etc.) and a tetravalent aromatic hydrocarbon (e.g. 1,4,5,8-naphthalenetetrayl, etc.), and an n-valent heterocyclic residue such as 2,4-furandiyl, 2,5-furandiyl, 2,5-thiophenediyl and 3,5-pyridinediyl, etc.

These organic groups include those which have been substituted with substituents such as a halogen atom, alkyl, aryl, heterocyclic, amino, nitro, cyano, carboxyl, hydroxy, alkoxy, aryloxy, acylamino, alkylcarbonyl, arylcarbonyl, alkylsulfonyl, arylsulfonyl, alkylthio or arylthio group.

These organic groups including the substituents are, for example, 1,2-dibromo-ethylene, 1-methoxy-2-hydroxy-ethylene, 1,2-dihydroxy-ethylene, hexafluoro-propylene, 2-phenyl-propylene, 2-pyridyl-propylene, 1-methyl-vinylene, 4-[butadiene (1,3)-1-yl]-1,5-pentenylene-(1), 3-methyl-propynylene, 3-cyano-1,2,4-butanetriyl, 5-nitro-1,3-phenylene, 5-butylamido-1,3-phenylene, 5-anilino-1,3-phenylene, 2-chloro-1,3,5-benzenetriyl, and 3,5,7-benzofuranetriyl.

Furthermore, the n-valent organic group represented by Z in accordance with the present invention includes an n-valent group in which the above-mentioned groups are mutually bonded, for example, a composite divalent group in which a divalent aliphatic hydrocarbon and arylene groups are bonded together, and a n-valent group in which the above-mentioned groups are bonded together through an oxygen atom, sulfur atom, selenium atom, sulfonyl or imino group.

These mutually bonded organic groups are preferably those represented by the following general formulas [IIa] and [IIb].

General formula [IIa]:

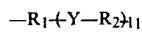

wherein $R_1$ and $R_2$ individually represent an n-valent organic group as above defined, preferably a divalent organic group, $l_1$ Y individually represents a single bond, an oxygen, sulfur or selenium bond, or a sulfonyl or imino group, which may be the same or different, and $l_1$ is an integer of from 1 to 4, preferably 1 or 2.

General formula [IIb]

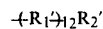

wherein $l_2$ $R_1'$ individually represents a single bond or a divalent bond or divalent organic group as above defined, which may be the same or different, and $R_2'$ represents an $l_2$-valent organic group, in the proviso that $l_2$ is 3 or more.

Further, the magenta couplers according to the present invention more preferably are those of the following general formula (IV).

General formula [IV]:

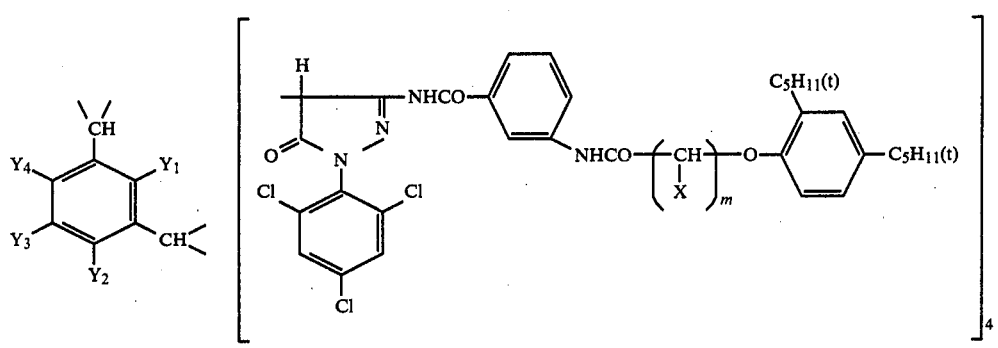

wherein X represents a hydrogen atom, or a methyl, ethyl, propyl or butyl group, $Y_1$, $Y_2$, $Y_3$ and $Y_4$ individually represent a hydrogen atom, a halogen atom such as chlorine and bromine, a hydroxy, nitro, cyano or amino group, an alkyl group such as methyl, ethyl, propyl, isopropyl, butyl, isobutyl, sec-butyl, tert-butyl, pentyl, hexyl, etc., or an alkoxy group such as methoxy, ethoxy, propoxy, isopropoxy, butoxy, isobutoxy, sec-butoxy, tert-butoxy, pentyloxy, hexyloxy, etc., and m is an integer of from 1 to 4.

Concrete examples of the compound having aldehydo groups, which is represented by the above-mentioned general formula [II], include, for example, such compounds as exemplified below.

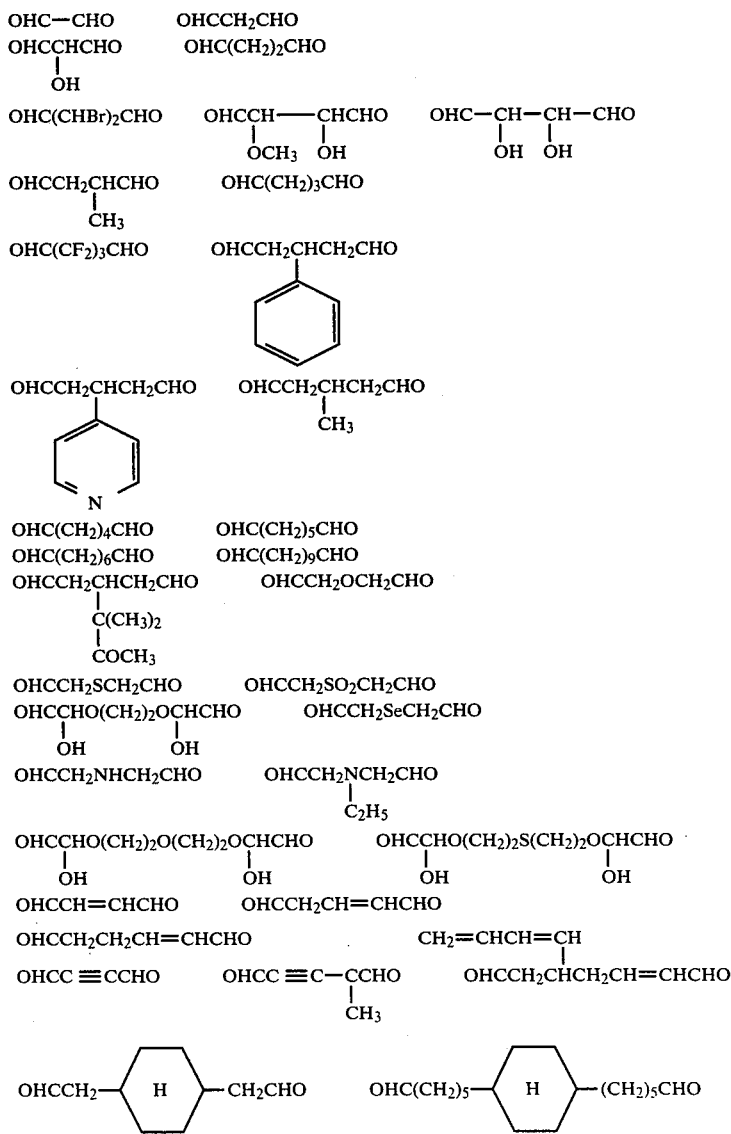

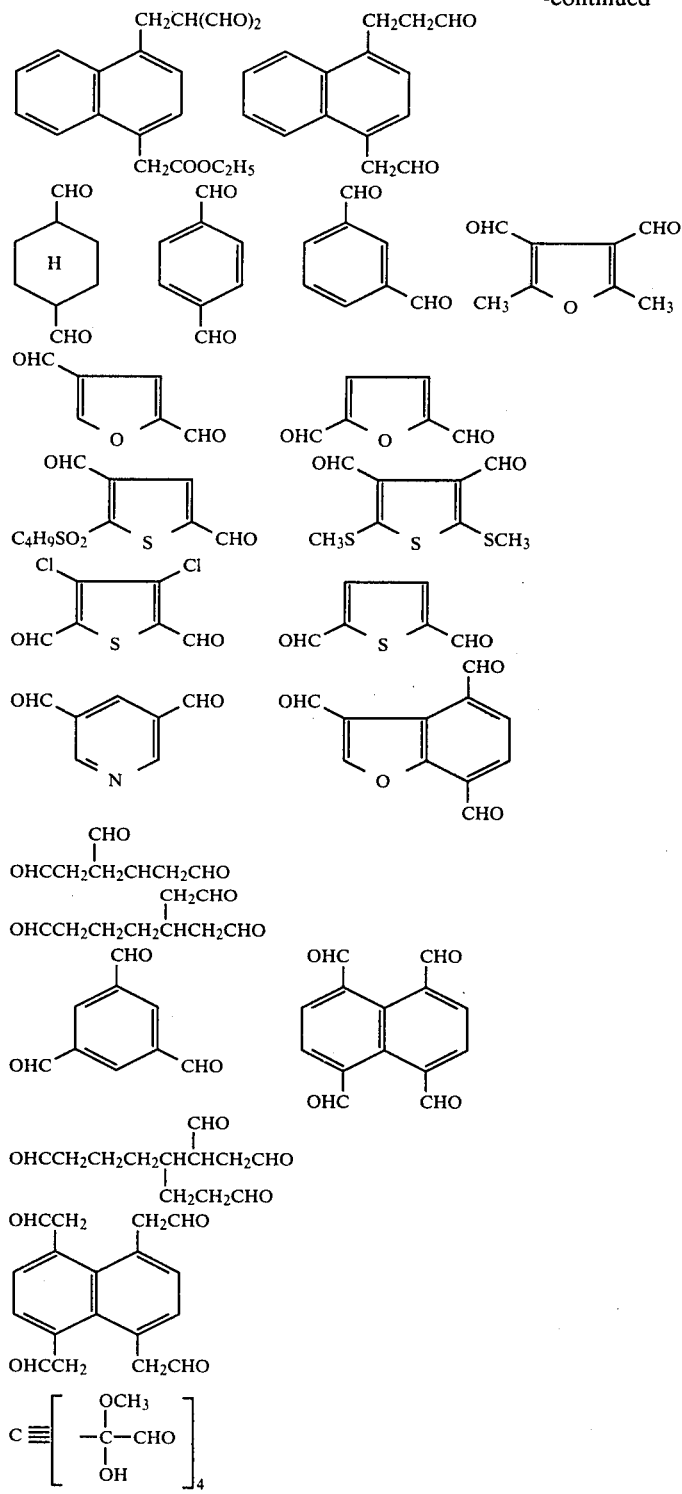

The above-mentioned compounds having aldehydo groups are well known from Beilstein's Library, etc. and readily prepared according to the procedure disclosed in said Library.

The magenta coupler used in the present invention, which has in the molecule at least four residues of the 5-pyrazolone compounds, from each of which one hydrogen atom at the 4-position has been removed, includes compounds represented by the following general formula [III].

General formula [III]

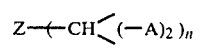

wherein A represents a residue of the 5-pyrazolone compound, from which one hydrogen atom at the 4-position has been removed, n represents an integer of 2 or more, and when n is 2, Z represents a single bond or a divalent organic group, and when n is 3 or more, Z represents an n-valent organic group.

In the above-mentioned general formula [III], A includes a residue of the compound having the formula [I] from which one hydrogen at the 4-position has been removed, and Z is as defined in Z of the aforesaid general formula [II].

The magenta couplers according to the present invention are preferably those of the aforesaid general formula [III] in which n is 2, 3 or 4, more preferably those in which n is 2. Concretely, the preferred magenta couplers used in the present invention include, for example, α,α,α',α'-tetrakis(3-acylamino-5-pyrazolone-4-yl)xylene, α,α,α',α'-tetrakis(3-anilino-5-pyrazolone-4-yl)xylene, α,α,α',α'-tetrakis(3-ureido-5-pyrazolone-4-yl)xylene and the like.

In the magenta coupler represented by the general formula [III], A which is a constituent member of said magenta coupler is not necessarily the same 5-pyrazolone compound in every case.

Typical examples which are not limitative but illustrative of the magenta coupler used in the present invention are given below. It should be construed in this connection that there may be used in the present invention any magenta couplers which are obtained by reaction of 5-pyrazolone compounds with compounds having aldehydo groups, provided that the magenta couplers obtained have in the molecule at least four residue of the pyrazolone compounds from which one hydrogen atom at the 4-position has been removed.

Cp - 1

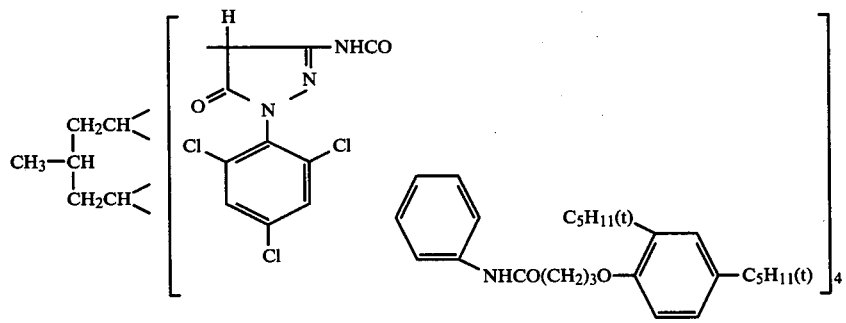

Cp - 2

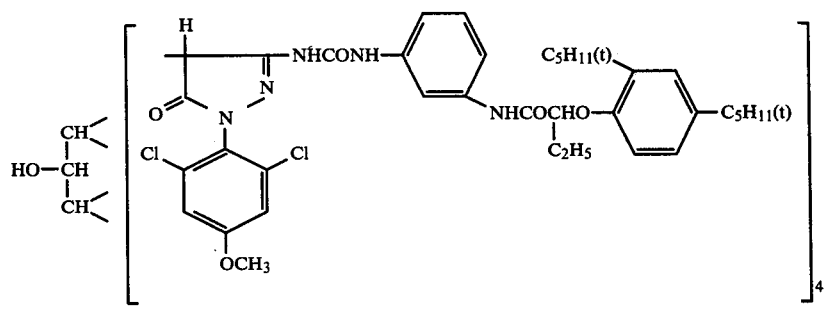

Cp - 3

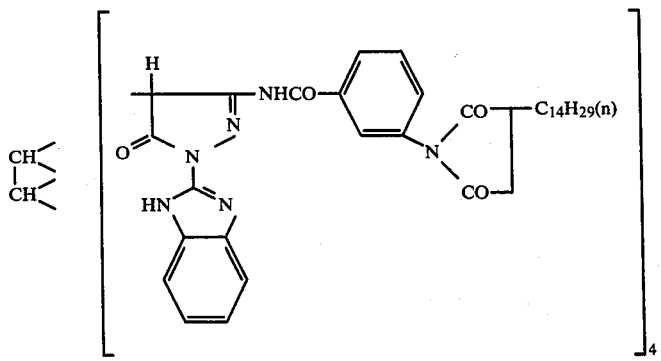

Cp - 4

-continued
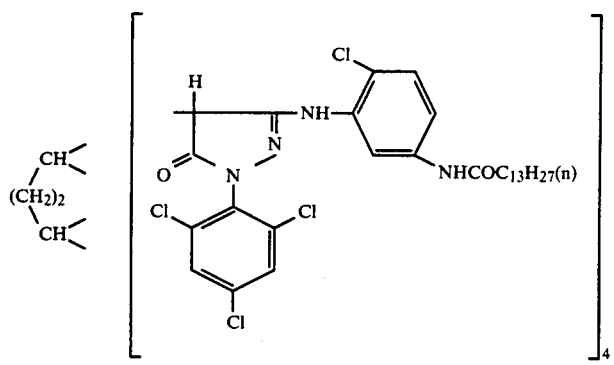
Cp - 5
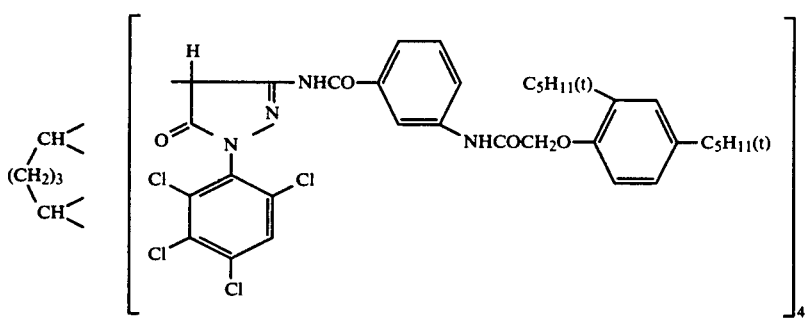
Cp - 6
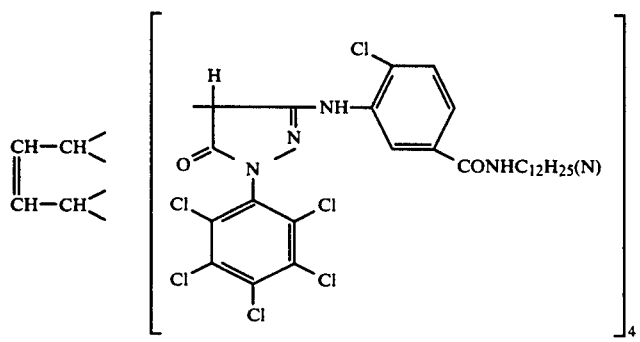
Cp - 7
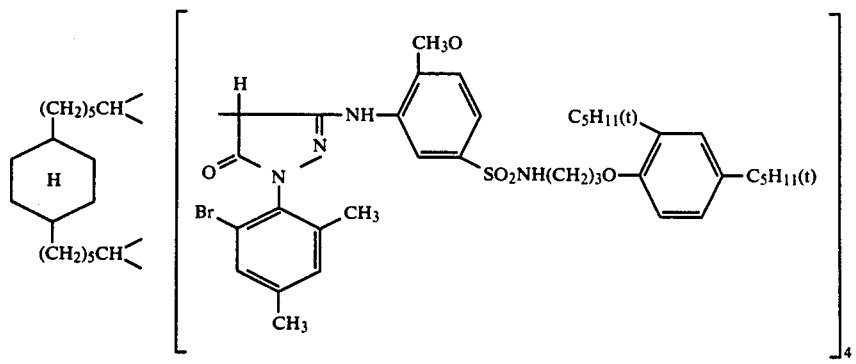
Cp - 8

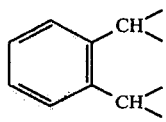
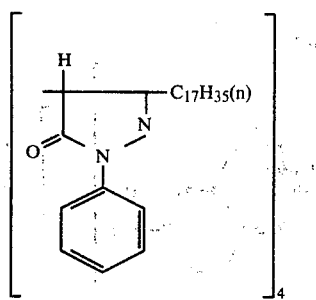
Cp - 9
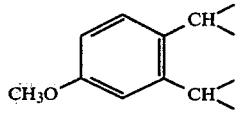
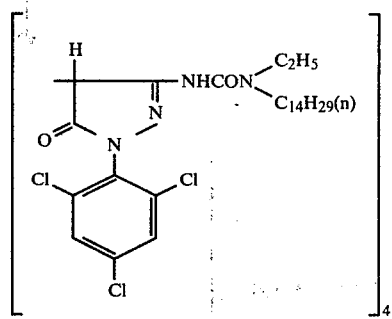
Cp - 10
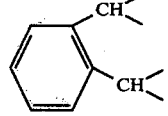
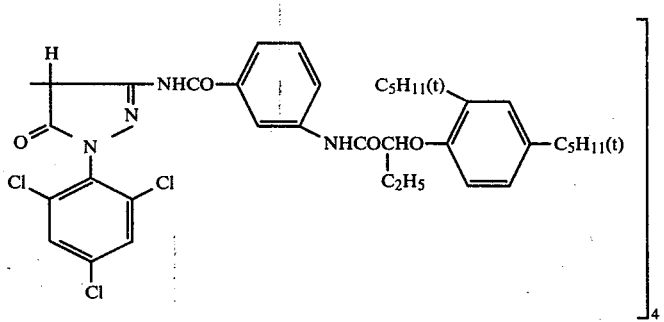
Cp - 11
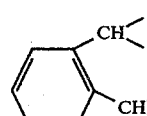
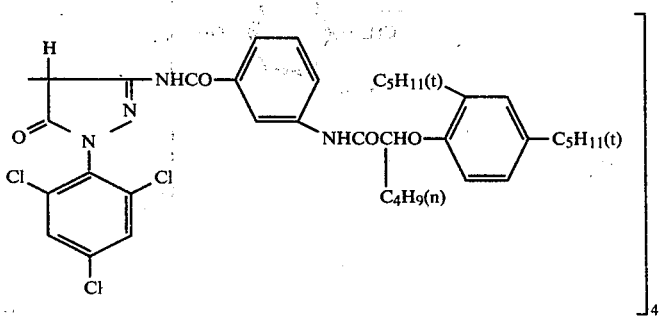
Cp - 12
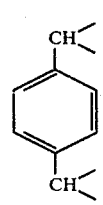
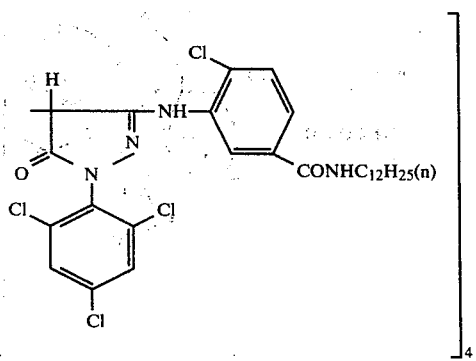
Cp - 13

-continued
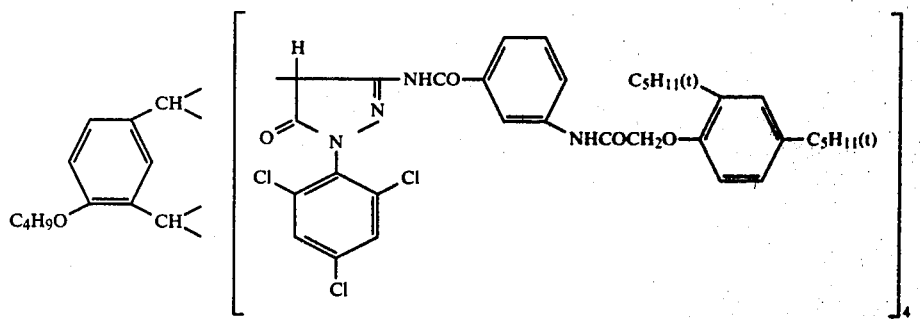
Cp - 14
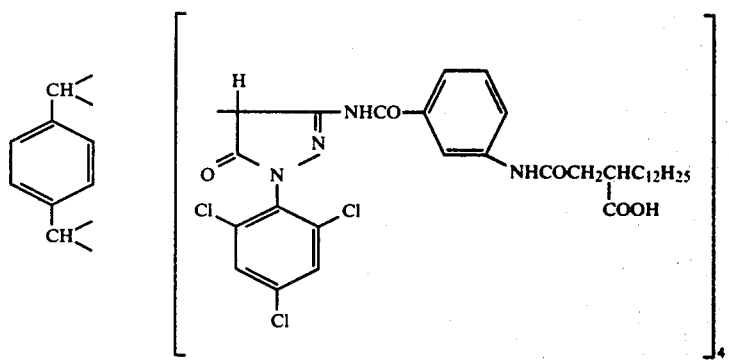
Cp - 15
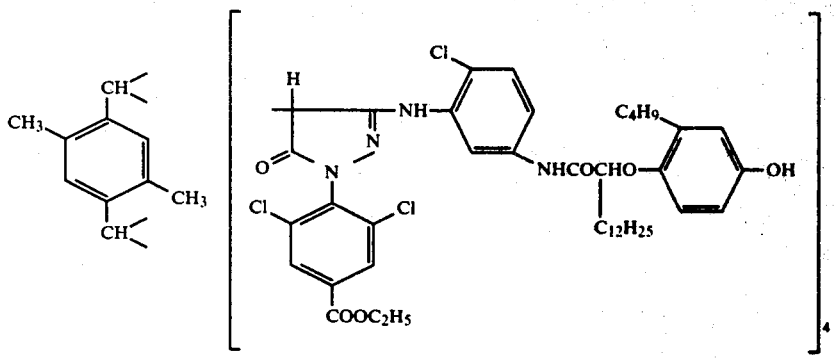
Cp - 16
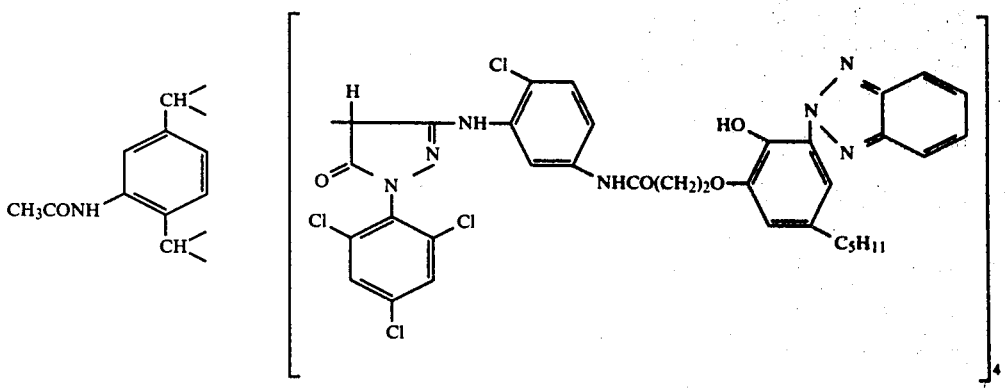
Cp - 17

-continued
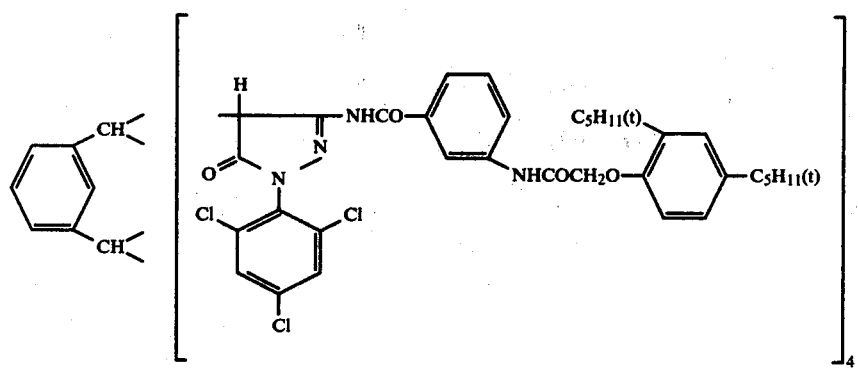
Cp - 18
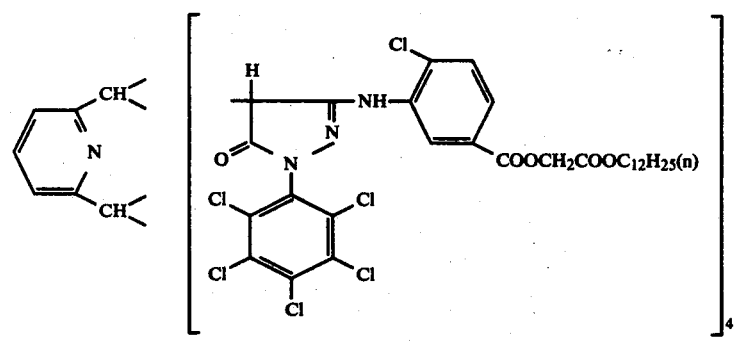
Cp - 19
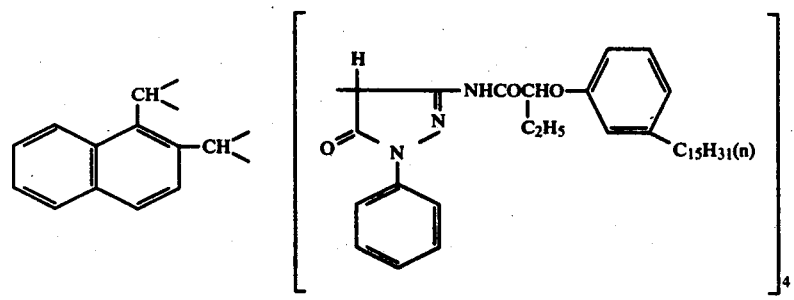
Cp - 20
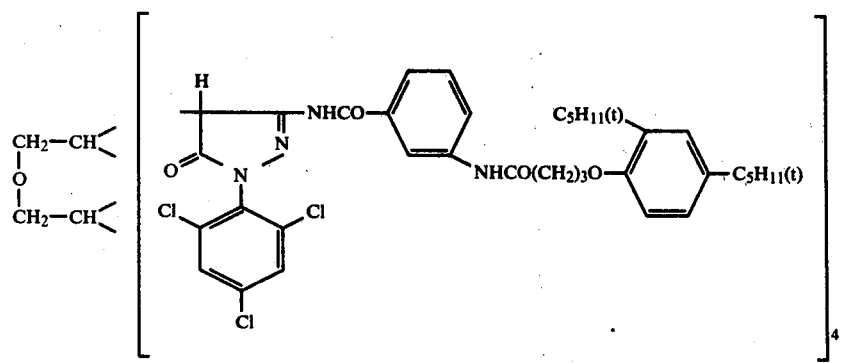
Cp - 21

-continued
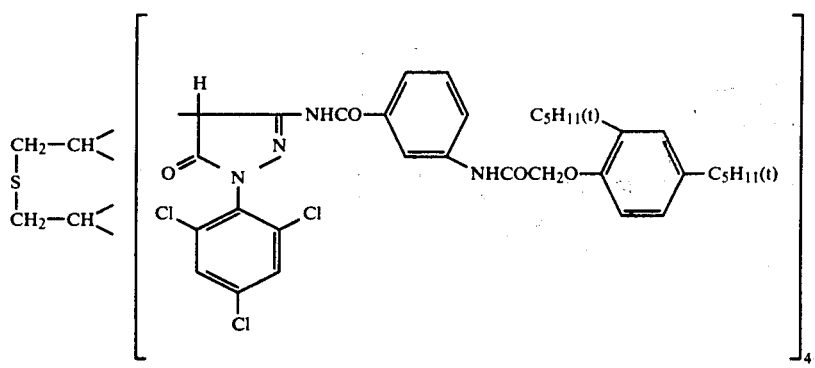
Cp - 22
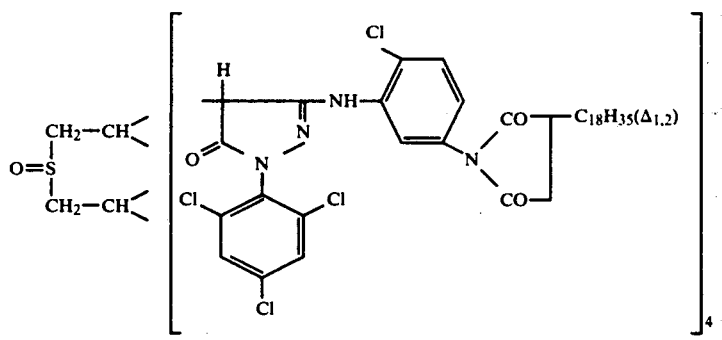
Cp - 23
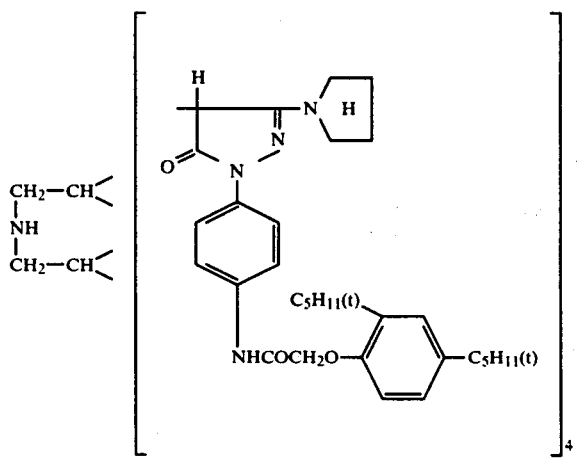
Cp - 24
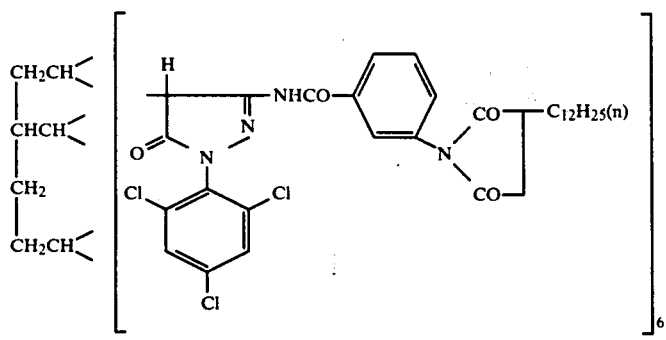
Cp - 25

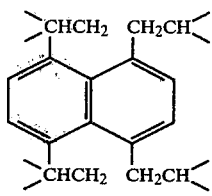 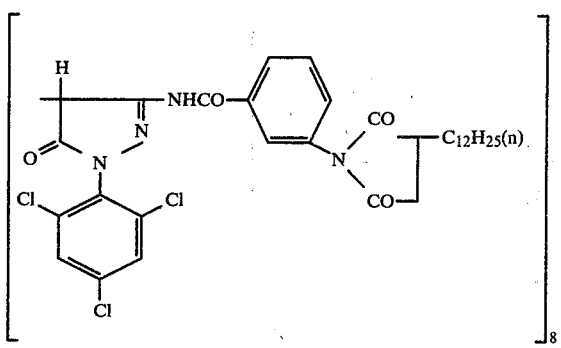
Cp - 26
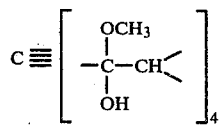 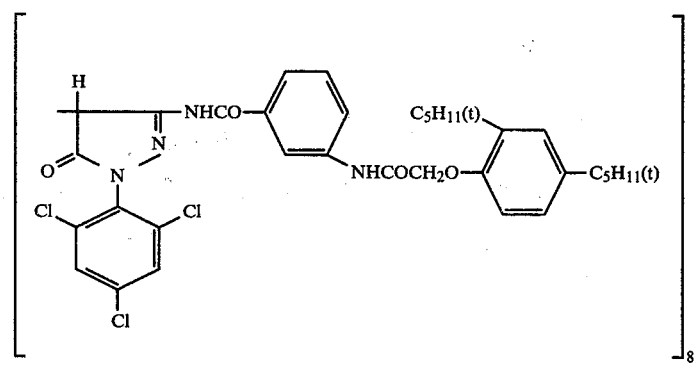
Cp - 27
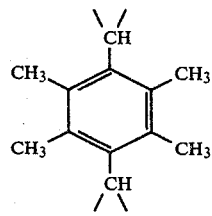 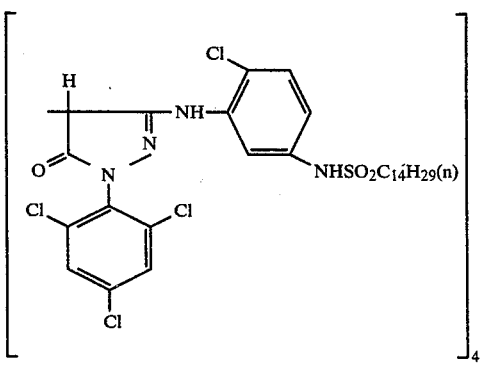
Cp - 28
 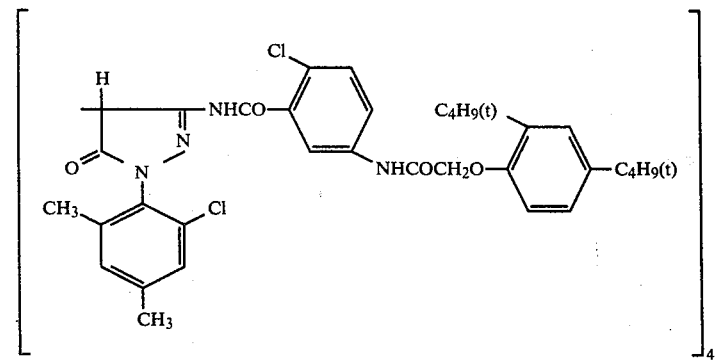
Cp - 29

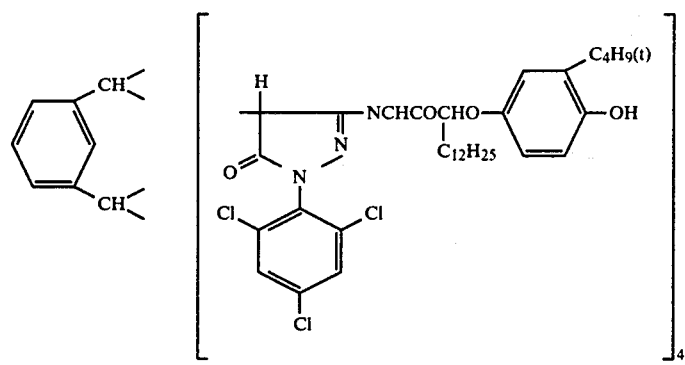
Cp - 30
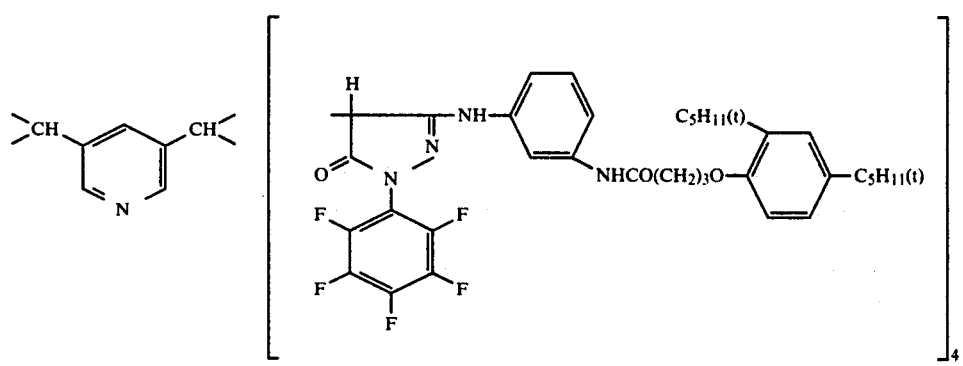
Cp - 31
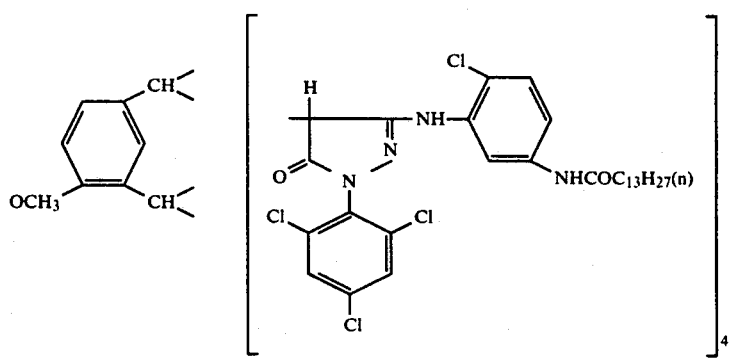
Cp - 32
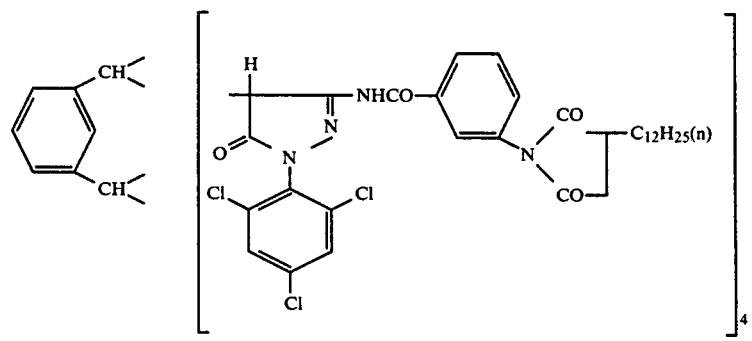
Cp - 33

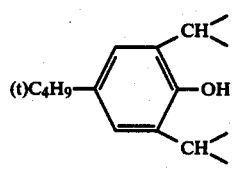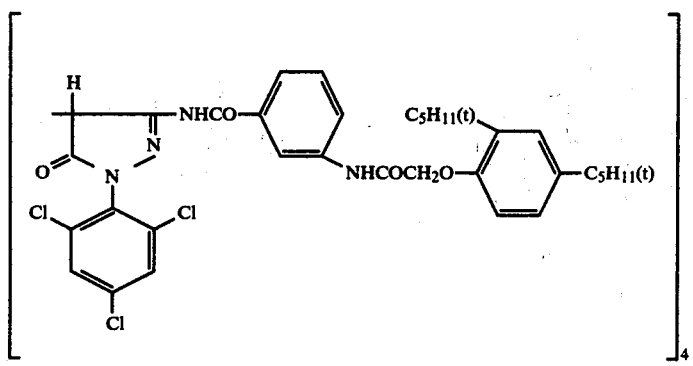
Cp - 34
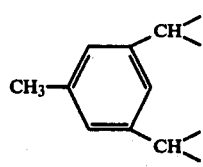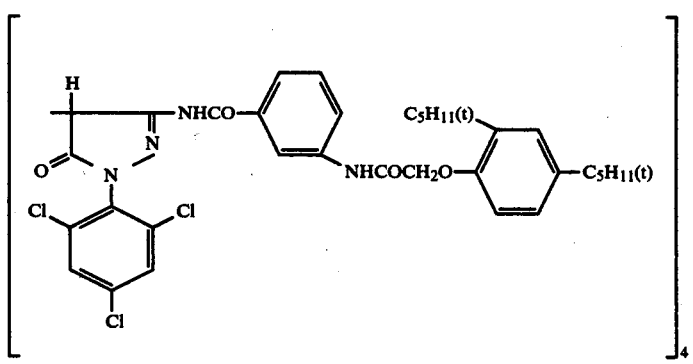
Cp - 35
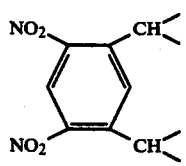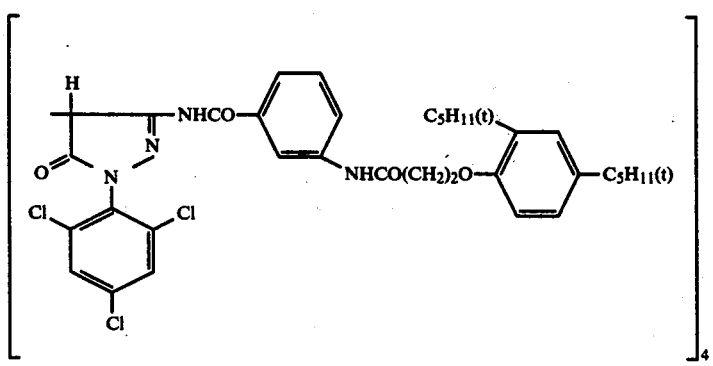
Cp - 36
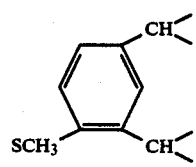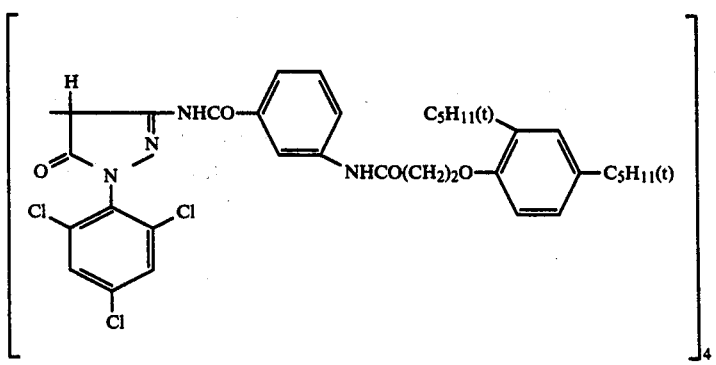
Cp - 37

-continued
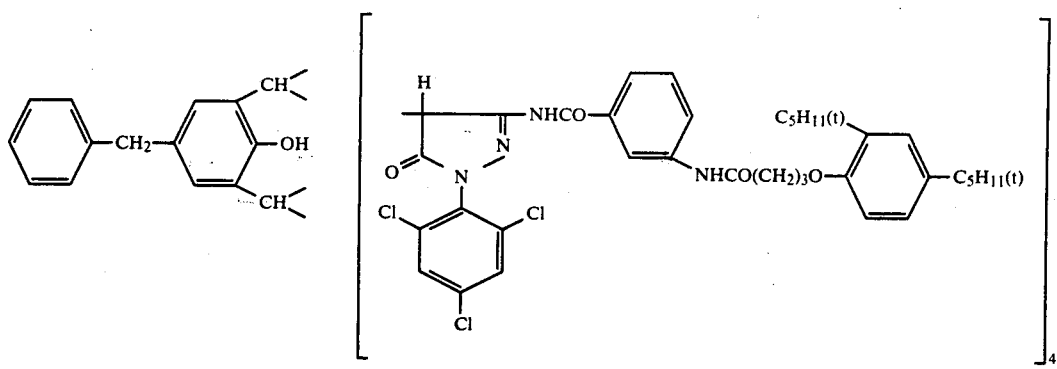
Cp - 38
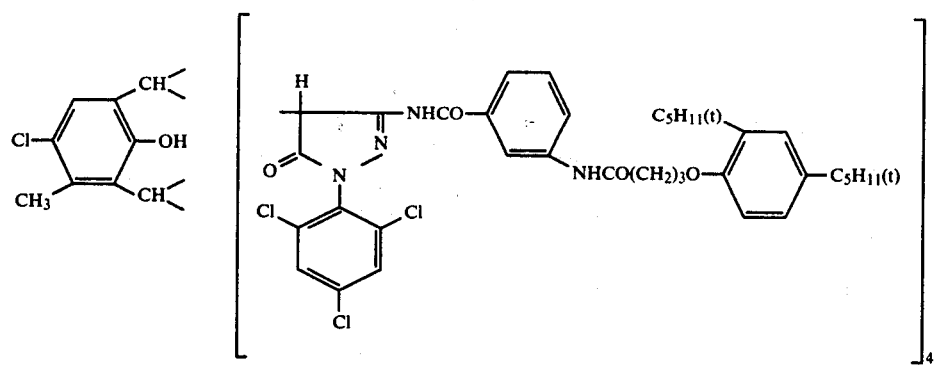
Cp - 39
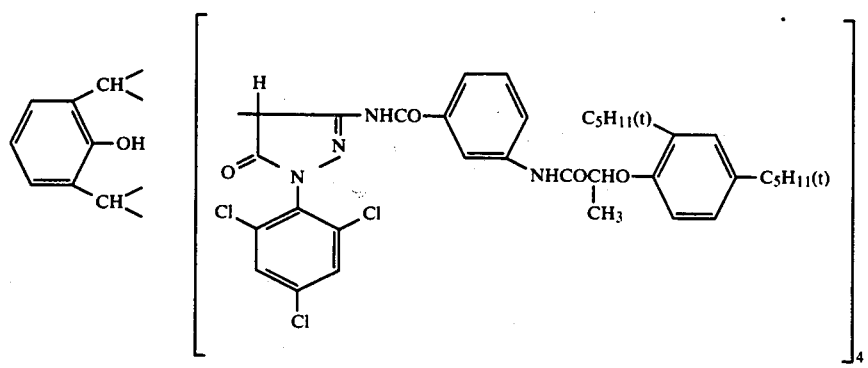
Cp - 40
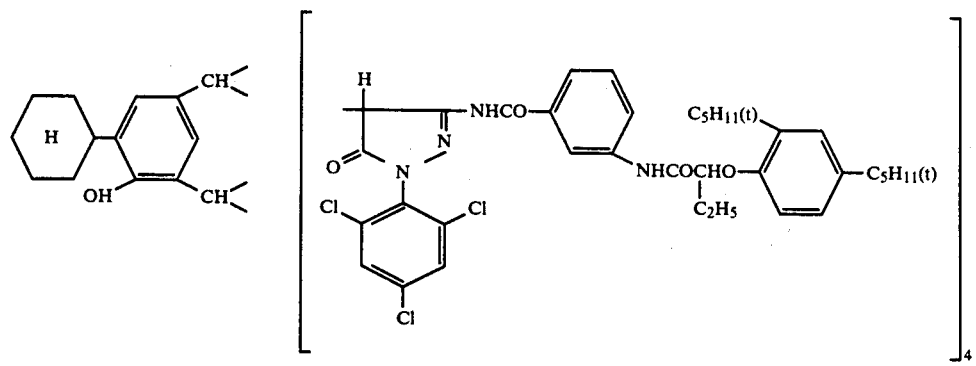
Cp - 41

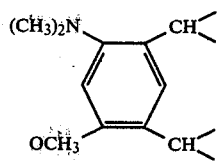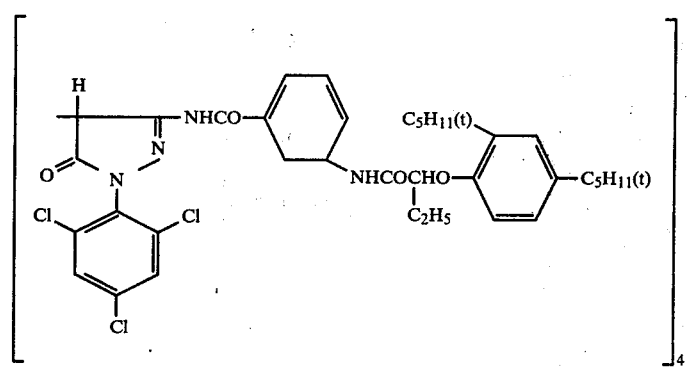
Cp - 42
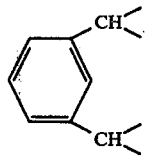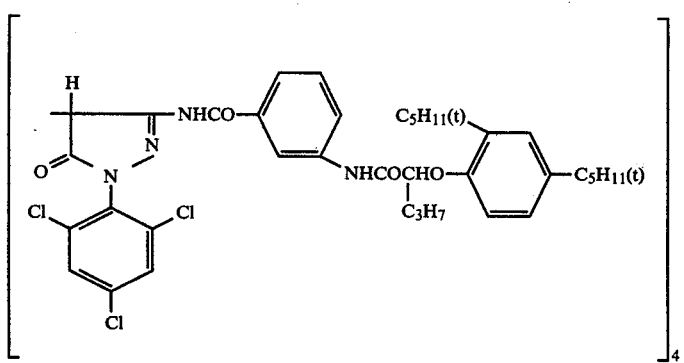
Cp - 43
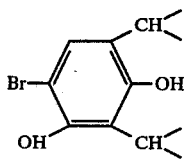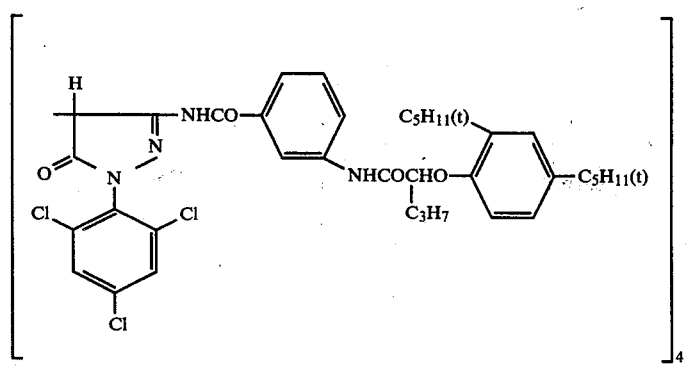
Cp - 44
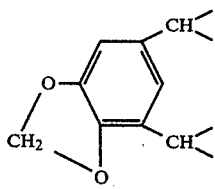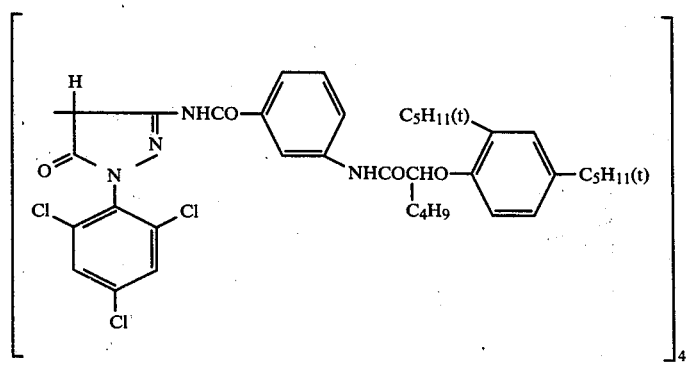
Cp - 45

-continued
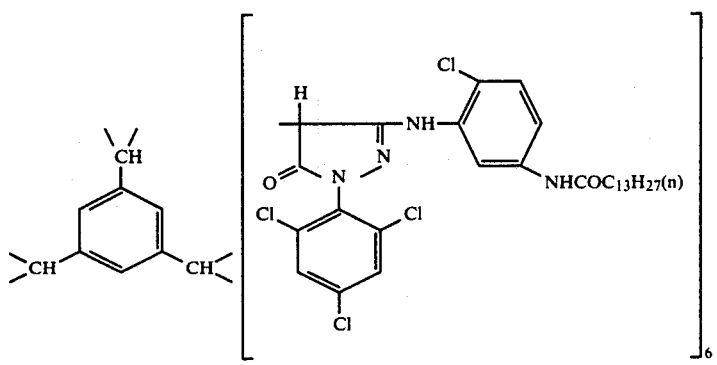
Cp - 46
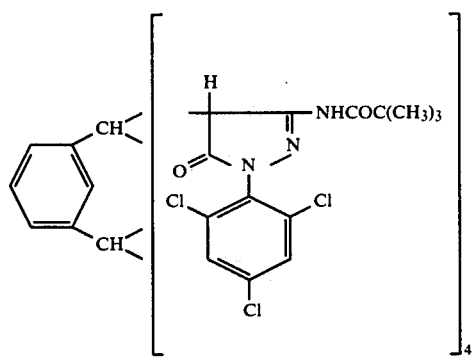
Cp - 47
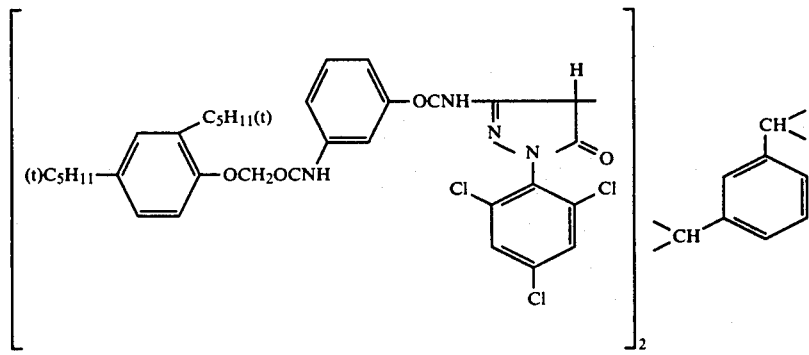
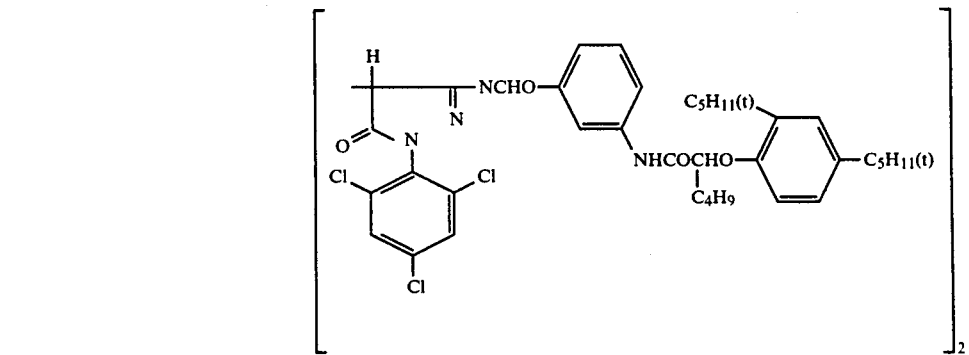
Cp - 48

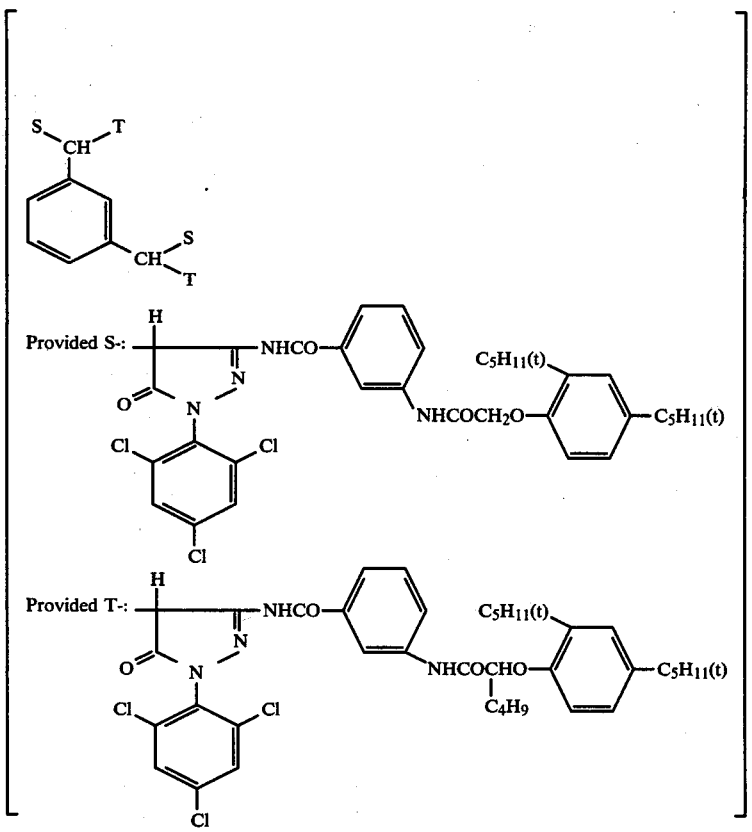

Prior to the preparation of magenta couplers used in the present invention, we first tried to allow 7.3 g (0.02 mole) of 1-(2,4,6-trichlorophenyl)-3-pivaloylamino-5-pyrazolone to react with 0.8 g (0.006 mole) of terephthalaldehyde, thereby to synthesize a compound of a relatively simple structure represented by the following structural formula.

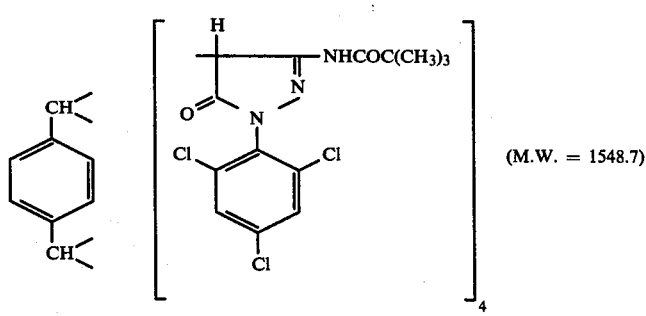

(M.W. = 1548.7)

That is, 7.3 g (0.02 mole) of 1-(2,4,6-trichlorophenyl)-3-pivaloylamino-5-pyrazolone was allowed to react with 0.8 g (0.006 mole) of terephthalaldehyde in 100 ml of ethanol for 16 hours with boiling under reflux. Thereafter, the reaction liquid was allowed to cool down to the liquid temperature of 50° C. and then white solids formed were collected by filtration and thoroughly rinsed with ethanol. The solids thus obtained were recrystallized from ligroin/chloroform to obtain a compound consisting of white amorphous crystals. Physical constants of the thus obtained compound measured were as shown below.

Melting point: 246°–250° C. (decomposition)
Molecular weight (measured by Hitachi 115 Type molecular weight measuring apparatus):

$1.58 \times 10^3$

NMR spectrum: $\delta CDU_3/DMSO\text{-}d_6$ 1.34(36H, singlet), 7.17(4H, singlet)
7.52(8H, singlet)
Elementary analysis (%)

|  | C | H | N | Cl |
|---|---|---|---|---|
| Calculated: | 49.63 | 3.77 | 10.85 | 27.47 |
| Found: | 49.30 | 3.98 | 10.81 | 27.25 |

From the experimental results as obtained above, it was judged that the compound obtained by the above-mentioned reaction is apparently the tetrakis body represented by the aforesaid structural formula.

Typical examples of the magenta coupler used in the present invention are explained below with reference to synthesis examples, but it should be construed that these examples are not of limitative but are of illustrative.

Synthesis Example 1 Preparation of exemplified coupler Cp-5

To a solution of 13,4 g of 1-(2,4,6-trichlorophenyl)-3-[3-{α-(2,4-di-tert-amylphenoxy)acetamido}benzamido]-5-pyrazolone in 200 ml of acetonitrile were added 2.0 g of a 25% aqueous glutaraldehyde and 2.0 g of triethylamine, and the resulting mixture was allowed to undergo reaction for 4 hours with boiling under reflux. Thereafter, the acetonitrile was distilled off under reduced pressure. The residue was dissolved in ethyl acetate, followed by water washing—dilute hydrochloric acid rinsing—water washing, and then dehydrated over sodium sulfate. The resultant solution was evaporated to dryness under reduced pressure and recrystallized from ethyl acetate to obtain the title compound consisting of white amorphous crystals, m.p. 184°–187° C. (decomposition).
Elementary analysis (%)

|  | C | H | N | Cl |
|---|---|---|---|---|
| Calculated: | 61.52 | 5.57 | 8.15 | 15.46 |
| Found: | 61.21 | 5.51 | 8.30 | 15.24 |

Synthesis Example 2 Preparation of exemplified coupler

Cp-10

To a solution of 14.0 g of 1-(2,4,6-trichlorophenyl)-3-[3-{α-(2,4-di-tert-amylphenoxy)butylamido}benzamido]-5-pyrazolone in 200 ml of ethanol was added 0.8 g of isophthalaldehyde, and the resulting solution was allowed to undergo reaction for 4 hours with boiling under reflux. After having allowed to cool down to room temperature, the reaction liquid was filtered to collect deposited solids, and the collected solids were thoroughly rinsed with ethanol to obtain the title compound consisting of white amorphous crystals, m.p. 190°–194° C. (decomposition).
Elementary analysis (%)

|  | C | H | N | Cl |
|---|---|---|---|---|
| Calculated: | 62.98 | 5.77 | 7.73 | 14.68 |
| Found: | 62.75 | 5.73 | 7.81 | 14.56 |

Synthesis Example 3 Preparation of exemplified coupler

Cp-12

To a solution of 12.0 g of 1-(2,4,6-trichlorophenyl)-3-{(2-chloro-5-n-dodecylcarbamoyl)anilino}-5-pyrazolone in 200 ml of isopropanol were added 0.8 g of terephthalaldehyde and 2.0 g of triethylamine, and the resulting mixture was allowed to undergo reaction for 2 hours with boiling under reflux. Thereafter, the reaction liquid was poured into dilute aqueous hydrochloric acid, and the deposited solids were collected by filtration, followed by thorough water washing, and was then dried. The solids thus collected were recrystallized from ligroin/ethanol to obtain the title compound consisting of white amorphous crystals, m.p. 174°–178° C. (decomposition).
Elementary analysis (%)

|  | C | H | N | Cl |
|---|---|---|---|---|
| Calculated: | 57.65 | 5.56 | 8.97 | 22.70 |
| Found: | 57.39 | 5.55 | 9.06 | 22.61 |

Synthesis Example 4 Preparation of exemplified coupler

Cp-17

To a solution of 13.4 g of 1-(2,4,6-trichlorophenyl)-3-[3-{α-(2,4-di-tert-amylphenoxy)acetamido}benzamido]-5-pyrazolone in 200 ml of ethanol was added 0.8 g of isophthalaldehyde, and the resulting mixture was allowed to undergo reaction for 5 hours with boiling under reflux. The reaction liquid was allowed to cool down to room temperature, and the deposited solids were then collected by filtration and thoroughly rinsed with ethanol to obtain the title compound consisting of white amorphous crystals, m.p. 262°–266° C. (decomposition).
Elementary analysis (%)

|  | C | H | N | Cl |
|---|---|---|---|---|
| Calculated: | 62.7 | 5.43 | 8.05 | 15.27 |
| Found: | 62.55 | 5.31 | 7.78 | 15.04 |

Synthesis Example 5 Preparation of 1-(2,4,6-trichlorophenyl)-3-[3-{α-(2,4-di-tert-amylphenoxy)acetamido}benzamido]-5-pyrazolone, 1-(2,4,6-trichlorophenyl)-3-[3-{α-(2,4-di-tert-amylphenoxy)hexanamido}benzamido]-5-pyrazolone and condensates thereof with isophthalaldehyde To a solution of 6.7 g of 1-(2,4,6-trichlorophenyl)-3-[3-{α-(2,4-di-tert-amylphenoxy)acetamido}benzamido]-5-pyrazolone and 7.3 g of 1-(2,4,6-trichlorophenyl)-3-[3-{α-(2,4-di-tert-amylphenoxy)hexanamido}benzamido]-5-pyrazolone in 200 ml of ethanol was added 0.7 g of isophthalaldehyde, and the resulting mixture was allowed to undergo reaction for 10 hours with boiling under reflux. Thereafter, the ethanol was distilled off under reduced pressure to obtain a caramel-like substance. It was confirmed that the object of the present invention can sufficiently be accomplished by the use of the thus obtained caramel-like substance.

Furthermore, the exemplified couplers other than those illustrated above can also be prepared according to procedures similar to those described in the foregoing Synthesis Examples.

| Exemplified coupler No. | Elementary analysis value (%) | | | | | |
|---|---|---|---|---|---|---|
|  | Calculated value | | | Found value | | |
|  | C | H | N | C | H | N |
| 1 | 62.59 | 5.95 | 7.79 | 62.38 | 5.91 | 7.86 |
| 2 | 62.65 | 6.27 | 9.68 | 62.60 | 6.14 | 9.45 |
| 3 | 68.96 | 7.09 | 13.59 | 68.79 | 6.92 | 13.48 |
| 4 | 57.47 | 5.87 | 8.94 | 57.61 | 5.97 | 8.77 |
| 5 | 61.52 | 5.57 | 8.15 | 61.21 | 5.51 | 8.30 |
| 6 | 51.12 | 4.73 | 8.22 | 51.03 | 4.80 | 8.22 |
| 7 | 62.08 | 7.03 | 6.98 | 62.24 | 7.12 | 7.17 |
| 8 | 79.47 | 10.12 | 6.62 | 79.29 | 10.03 | 6.75 |
| 9 | 58.70 | 6.98 | 9.69 | 58.82 | 6.94 | 9.79 |
| 10 | 62.98 | 5.77 | 7.73 | 62.75 | 5.73 | 7.81 |

-continued

| Exemplified coupler No. | Calculated value | | | Found value | | |
|---|---|---|---|---|---|---|
| | C | H | N | C | H | N |
| 11 | 63.83 | 6.09 | 7.44 | 64.00 | 6.01 | 7.63 |
| 12 | 57.65 | 5.56 | 8.97 | 57.39 | 5.55 | 9.06 |
| 13 | 62.19 | 5.57 | 7.84 | 62.16 | 5.63 | 7.94 |
| 14 | 59.13 | 5.77 | 8.11 | 59.28 | 5.92 | 8.21 |
| 15 | 63.04 | 6.48 | 6.61 | 62.95 | 6.40 | 6.66 |
| 16 | 59.35 | 4.28 | 13.38 | 59.27 | 4.33 | 13.52 |
| 17 | 62.07 | 5.43 | 8.05 | 62.55 | 5.31 | 7.78 |
| 18 | 50.63 | 4.45 | 6.05 | 50.42 | 4.69 | 5.86 |
| 19 | 75.99 | 8.62 | 7.19 | 76.19 | 8.81 | 7.12 |
| 20 | 62.01 | 5.84 | 7.82 | 62.29 | 5.70 | 7.80 |
| 21 | 60.69 | 5.46 | 8.09 | 60.53 | 5.29 | 7.89 |
| 22 | 59.96 | 6.16 | 7.36 | 59.71 | 6.02 | 7.54 |
| 23 | 71.84 | 8.06 | 11.13 | 71.94 | 8.17 | 11.06 |
| 24 | 60.11 | 5.73 | 8.46 | 59.88 | 5.56 | 8.45 |
| 25 | 60.84 | 5.67 | 8.29 | 60.61 | 5.54 | 8.11 |
| 26 | 60.34 | 5.47 | 7.90 | 60.33 | 5.28 | 7.99 |
| 27 | 54.66 | 5.81 | 7.97 | 54.90 | 5.75 | 7.78 |
| 28 | 64.64 | 5.81 | 8.49 | 64.47 | 5.80 | 8.61 |
| 29 | 60.11 | 5.97 | 6.87 | 60.33 | 5.89 | 6.76 |
| 30 | 61.48 | 5.37 | 8.29 | 61.47 | 5.15 | 8.41 |
| 31 | 58.06 | 5.77 | 8.67 | 58.00 | 5.98 | 8.52 |
| 32 | 60.72 | 5.62 | 8.33 | 60.61 | 5.47 | 8.16 |
| 33 | 62.19 | 5.57 | 7.84 | 62.36 | 5.44 | 7.93 |
| 34 | 62.19 | 5.47 | 8.00 | 62.38 | 5.36 | 8.10 |
| 35 | 60.62 | 5.36 | 8.60 | 60.81 | 5.42 | 8.53 |
| 36 | 61.95 | 5.58 | 7.76 | 62.13 | 5.50 | 7.71 |
| 37 | 63.56 | 5.77 | 7.46 | 63.40 | 5.69 | 7.68 |
| 38 | 62.02 | 5.68 | 7.56 | 61.91 | 5.62 | 7.75 |
| 39 | 62.19 | 5.57 | 7.84 | 62.19 | 5.43 | 7.99 |
| 40 | 63.32 | 5.92 | 7.48 | 63.47 | 5.81 | 7.68 |
| 41 | 62.65 | 5.87 | 8.01 | 62.90 | 5.98 | 8.17 |
| 42 | 63.41 | 5.94 | 7.59 | 63.38 | 6.16 | 7.75 |
| 43 | 61.12 | 5.69 | 7.51 | 60.86 | 5.55 | 7.14 |
| 44 | 63.28 | 6.04 | 7.33 | 63.41 | 5.94 | 7.54 |
| 45 | 57.92 | 5.74 | 8.86 | 57.73 | 5.92 | 8.87 |
| 46 | 49.63 | 3.77 | 10.85 | 49.87 | 3.66 | 10.72 |
| 47 | 62.98 | 5.77 | 7.73 | 62.73 | 5.70 | 7.85 |
| 48 | 62.98 | 5.77 | 7.73 | 62.79 | 5.91 | 7.74 |

In forming magenta dye images by the use of magenta couplers according to the present invention, there may be employed any of two means, i.e. the so-called inner type method wherein said magenta coupler is incorporated into a light-sensitive silver halide photographic material and the so-called outer type method wherein said magenta coupler is incorporated into a color developer. In the case where the inner type method is employed, the magenta coupler of the present invention may be incorporated into a silver halide emulsion by first dissolving said coupler in a high boiling organic solvent having a boiling point of 175° C. or higher or in a low boiling organic solvent, or a mixture thereof. The high boiling organic solvent include, for example, dibutyl phthalate, dioctyl phthalate, triphenyl phosphate, tricresyl phosphate, phenoxy ethanol, diethylene glycol monophenylether, diethoxyethyl phthalate, diethyl laurylamide or dibutyl laurylamide, and the low boiling organic solvent includes, for example, ethyl acetate, butyl acetate, methanol, ethanol, butanol, acetone, β-ethoxyethyl acetate, methoxytriglycol acetate, dioxane or fluorinated alcohol. Thereafter, the magenta coupler solution is mixed with an aqueous gelatin solution containing a surface active agent, and the mixture is treated by means of a high speed rotary mixer or a colloid mill to obtain an emulsified dispersion of the magenta coupler which is then incorporated directly into the silver halide emulsion. Alternatively, the said emulsified dispersion is set and then finely divided into needles which are then incorporated, after removing the low boiling organic solent therefrom by such means as water-washing, into the silver halide emulsion. The magenta couplers which are soluble in alkali may be incorporated according to the so-called Fischer's dispersion technique into the silver halide emulsion. The amount of the magenta coupler to be incorporated in accordance with the present invention, in general, is preferably 10–300 g per mole of silver halide present in a silver halide emulsion, though said amount may of course be varied according to the kind of magenta coupler used, the purpose for which the coupler is used and so forth.

In the light-sensitive silver halide color photographic materials incorporated with the magenta couplers of the present invention, not only yellow and cyan couplers for the purpose of forming other dye images can be used in combination with the present magenta couplers but also various photographic additives can be used together. Yellow couplers preferably usable in combination with the present magenta couplers include benzoyl acetanilide type yellow couplers, pivaloyl acetanilide type yellow couplers, or 2-equivalent type yellow couplers, of which the carbon atom at the coupling position has been substituted by a substituent which are capable of being released at the time of coupling reaction.

As cyan couplers preferably usable in combination with the present magenta couplers, there may be mentioned phenol- or naphthol-derivatives. Furthermore, as colored cyan couplers usable for the same purpose, there may be mentioned such compounds, which are colorless cyan couplers having their coupling position been substituted by an arylazo group, or colored cyan couplers of the type, of which the dye formed by the reaction with an oxidation product of a color developing agent comes to flow into a processing bath.

Still further, in the light-sensitive silver halide color photographic materials in which the magenta couplers of the present invention are used, there may be, if necessary, magenta couplers of other types in combination with the present magenta couplers. Concretely, such magenta couplers of the other types include compounds of pyrazolone-, pyrazolotriazole-, pyrazolobenzimidazole- or indazolone-type, and colored magenta couplers, concretely such compounds, of which the coupling position of colorless magenta coupler has been substituted by an arylazo group, or colored magenta couplers of the type, of which the dye formed on reaction with an oxidation product of a color developing agent comes to flow into a processing solution. Even in the case where the magenta couplers of the present invention are used in combination of two or more in a light-sensitive silver halide color photographic material, there is obtained an excellent color photographic material.

Particularly, when magenta couplers, which have been found to be satisfactory in respect of color forming rate but found to be poor in property resisting to formalin gas, are used in combination with the present magenta couplers in a light-sensitive silver halide color photographic material, the color photographic material obtained thereby is found to be excellent in both color forming rate and property resisting to formalin gas.

Further, it is possible to use development inhibitor-releasing type couplers (so-called DIR couplers) or development inhibitor-releasing type substances which do not form dyes on reaction with an oxidation product of a developing agent for the purpose of improving sharpness, graininess, etc. of color image, and these couplers or substances may be used either singly or in combination of two or more.

The couplers and the like compounds hereinbefore mentioned can be used in combination of two or more in the same one layer for satisfying the characteristics required for light-sensitive material, or they can be used singly in two or more different layers, as well.

In the light-sensitive silver halide color photographic materials to which the present invention is applied, hydrophilic colloid which is advantageously usable for preparing photosensitive emulsions includes gelatin, gelatin derivatives such as phenylcarbamylated gelatin, amylated gelatin, phthalated gelatin, etc., colloidal albumin, agar, gum arabic, cellulose derivatives such as hydrolyzed cellulose acetate, carboxymethylcellulose, hydroxyethylcellulose, methylcellulose, etc., acrylamide, imidated polyacrylamide, casein, vinyl alcohol polymers containing urethanecarboxylic acid group or cyanoacetyl group such as vinyl alcohol/vinyl cyanoacetate copolymers, polyvinyl alcohol, polyvinyl pyrrolidone, hydrolyzed polyvinyl acetate, and polymers obtained by polymerization of protein or saturated acylated protein with monomers having vinyl groups. Silver halide used in the photosensitive emulsions includes any silver halides commonly used in silver halide photographic emulsions such as silver bromide, silver chloride, silver iodobromide, silver chlorobromide, silver chloroiodobromide, etc.

Particles of these silver halides may be either of coarse or fine grain, and the distribution of particle diameter may be either narrow or broad.

The crystal form of these silver halide grains may be either normal or twin, and the face ratio of [1.0.0] to [1.1.1] may be optionally selected.

The crystal structure of these silver halide grains may be either such that the structure is homogeneous from the inside to the outside or such that the stratum structure of the inside is different from that of the outside.

These silver halides may be either of the type which mainly form latent images on the surface thereof or of the type which form latent images in the inside of grains thereof.

Silver halide emulsions used in light-sensitive silver halide color photographic materials in accordance with the present invention may be prepared according to various procedures, including of course such procedures as commonly used in the art. For instance, such procedure as disclosed in Japanese Patent Publication No. 7772/1971 or such procedure as disclosed in U.S. Pat. No. 2,592,250 may be adoptable, i.e. the procedure for preparing the so-called conversion emulsion, wherein an emulsion of silver salt particles consisting of at least a part of silver salt having a solubility greater than that of silver bromide is prepared and then at least a part of said particles are converted into silver bromide salt or silver iodobromide salt, or the procedure for preparing Lippmann's emulsion comprising fine-grained silver halide having an average particle diameter of less than $0.1\mu$.

The silver halide emulsions prepared in the manner explained above can be sensitized with chemical sensitizers. The chemical sensitizers are roughly classified into four groups, i.e. noble metal sensitizers, sulfur sensitizers, selenium sensitizers and reduction sensitizers.

The noble metal sensitizers include gold compounds and compounds of ruthenium, rhodium, palladium, iridium and platinum. Particularly preferable compounds are chloroauric acid, potassium chloroaurite, potassium aurithiocyanate, potassium chloroaurate, 2-auro-sulfobenzothiazole methylchlorite, ammonium chloropalladate, potassium chloroplatinate, sodium chloropalladite and sodium chloroiridate. When the gold compounds are used, ammonium thiocyanate or sodium thiocyanate may be used in combination therewith.

The sulfur sensitizers include sulfur compounds in addition to active gelatin, and particularly preferable compounds are sodium thiosulfate, ammonium thiosulfate, thiourea, thioacetamide, allyisothiourea, N-allylrhodanine, etc.

The selenium sensitizers include active and inactive selenium compounds, and particularly preferable compounds are colloid selenium, selenoacetophenone, selenoacetamide, selenourea, N,N-dimethylselenourea, triphenylphosphine selenide, etc.

The reduction sensitizers include monovalent tin salts, polyamines, bisalkylaminosulfides, silane compounds, iminoaminomethanesulfinic acid, hydrazinium salts and hydrazine derivatives.

The photographic emulsions can be color hypersensitized, if necessary, according to spectral sensitization by the use of cyanine dyes such as cyanine, merocyanine, carbocyanine, etc., either singly or in combination, or by the use of said cyanine dyes in combination with styryl dyes.

Selection of the sensitizer may be optionally made according to the object for which the light-sensitive silver halide color photographic material is intended to be used, such as a wavelength region to be sensitized, sensitivity, etc. of the intended photographic material.

In order to prevent light-sensitive silver halide color photographic materials form the drop in sensitivity or formation of fog during the production step, storage of processing thereof, the above-mentioned silver halide emulsions can be incorporated with various compounds, for example, heterocyclic compounds such as 1-phenyl-5-mercaptotetrazole, 3-methylbenzothiazole, 4-hydroxy-6-methyl-1,3,3a,7-tetrazaindene, etc. mercapto compounds and metal salts.

Film hardening treatment of the photographic emulsion is carried out according to the usual method. Hardeners used in this treatment include ordinary photographic hardeners, for example, aldehyde type compounds such as formaldehyde, glyoxal and glutaraldehyde and their derivatives such as acetal- or sodium bisulfite-addition products, methanesulfonic acid ester type compounds, mucochloric acid or mucohalogen acid type compounds, epoxy type compounds, aziridine type compounds, active halogen type compounds, maleic acid imide type compounds, active vinyl type compounds, carbonimide type compounds, isooxazole type compounds, N-methylol type compounds, isocyanate type compounds or inorganic hardeners such as alum chromate, zirconium sulfate, etc.

The above-mentioned silver halide emulsions may be incorporated with surface active agents, either singly or in admixture thereof.

The surface active agents which are used as agents for improving permeability to coating aids, emulsifiers, processing solutions, etc., and as defoaming agents, antistatic agents, anti-adhesion agents and materials for improving photographic properties or controlling physical properties. Usable as the surface active agents as mentioned above include natural products such as saponin, non-ionic surfactants of alkylene oxide type, glycerine type and glycidol type, cation surfactants such as higher alcohols, pyridine, other heterocycles, quaternary nitrogen onium salts, phosphonium or sulfonium salts, anion surfactants containing acid groups such as carboxylic acid, sulfonic acid, phosphoric acid, sulfate or phosphate group, and amphoteric surfactants such as amino acids and aminosulfonic acids.

The light-sensitive silver halide color photographic materials of the present invention may contain in constitutive layers thereof (e.g. protective layer, intermediate layer, emulsion layer, backing layer, etc.) benzotriazoles, triazines, benzophenone type compounds or acrylonitrile type compounds as ultraviolet absorbers. Particularly preferable ultraviolet absorbers are products of Ciba-Geigy Co., for example, Thinubin Ps, 320, 326, 327 and 328, which are used either singly or in combination.

For the purpose of stabilizing the resulting color photographs, moreover, p-phenols can be incorporated into emulsion layers and/or adjacent layers of light-sensitive silver halide color photographic materials to which the present invention is applied. Particularly preferable p-substituted phenols include alkyl-substituted hydroquinones, bis-hydroquinones, polymer type hydroquinones, p-alkoxyphenols, phenolic compounds, etc. Further, alkoxy or amyloxy derivatives of 6-chromanol or 6,6'-dihydroxy-2,2'-spirochroman may similarly be used.

The light-sensitive silver halide color photographic materials are prepared by coating their constitutive layers on a support excellent in flatness and less liable to dimentional change during the production step or processing thereof. Usable as the support in that case, is a film of cellulose acetate, cellulose nitrate, polyvinyl acetal, polypropylene, polyethylene terephthalate, polyamide, polycarbonate, polystyrene, etc., or polyethylene-laminated paper, synthetic paper made of polypropylene, baryta paper, etc. These supports may be suitably selected according to the object for which the desired light-sensitive silver halide color photographic material is used.

In order to provide a strong adhesion between a silver halide emulsion layer and a support, generally the above-mentioned supports are subjected to subbing treatment. Typical subbing materials used in the subbing treatment of supports are copolymerized products of vinyl chloride or vinylidene chloride, copolymerized products of esters of vinyl alcohol, copolymerized products containing unsaturated carboxylic acids, copolymerized products of dienes such as butadiene, copolymerized products of acetals, copolymerized products of anhydrides of unsaturated carboxylic acids such as maleic acid particularly with vinyl alcohol esters such as vinyl acetate or styrene, or ring-opened bodies thereof obtained by the use of water, alkali, alcohols or amines, cellulose derivatives such as nitrocellulose, diacetylcellulose, etc., compounds containing epoxy groups, gelatin or modified gelatin products, and polyolefin copolymerized products.

Further, the subbing treatment can also be carried out by the use of gelatin or polyols, monovalent or polyvalent phenols and halogen-substituted bodies thereof, cross-linking agents (film hardeners), metal oxides, etc. in combination with the above-mentioned subbing materials.

In actually practicing the subbing treatment of support, the above-mentioned subbing materials can be used, either singly or in combination. In the subbing treatment, a single or multi-coated subbing layer can be formed on a support, and such subbing layer may be further coated on the surface with said subbing materials to form a multi-coated subbing layer on the support. For example, there is adopted a method wherein a gelatin layer is further coated on a layer comprising the copolymerized product of vinylidene chloride, or a method wherein a layer comprising the copolymerized product of vinylidene chloride, a layer comprising a mixture of gelatin and the copolymerized product of vinylidene chloride and a gelatin layer are coated in that order on a support. In these method, any combination use of subbing materials can be employed and a combination of these methods can be adopted to form a multi-coated subbing layer on a support.

Besides the above-mentioned subbing treatment using such subbing materials explained previously, there can be attained adhesion between a support and an emulsion layer by subjecting the support on its surface to such treatment as corona discharge, glow discharge, other electron bombardment, flame treatment, ultraviolet irradiation, oxidation treatment, saponification treatment or surface roughening treatment. These treatments can be employed, either singly or in combination, and a more sufficient subbing treatment can be carried out by employing any of these treatments in combination with the aforesaid subbing treatment using subbing materials.

The light-sensitive silver halide color photographic materials to which the present invention is applied include light-sensitive silver halide color photographic materials of every kind, such as color negative films, color positive films, color reversal films, color papers, etc.

The light-sensitive silver halide color photographic materials to which the present invention is applied are advantageously color developed, after imagewise exposure to light, preferably according to common color development technique employed for processing the so-called inner type light-sensitive silver halide color photographic materials, though the so-called outer color processing method may be applied thereto, if necessary.

When the outer color processing method is employed in the present invention, a color developer having the composition, for example, such as in the following, may be used.

| | |
|---|---|
| 4-Amino-3-methyl-N-ethyl-N-($\beta$-methanesulfonamidoethyl)-aniline sulfate | 5.0 g |
| Sodium sulfite | 2.0 g |
| Benzyl alcohol | 3.5 ml |
| Sodium carbonate | 82 g |
| Potassium bromide | 1.0 g |
| Coupler | 0.005 mole |
| Water to make | 1 liter |

When the inner type color processing method is employed in the present invention, the above-mentioned outer type color developer from which the coupler has been omitted may be used as an inner type color developer, and the inner type color developer is subjected to pH adjustment according to the object and simultaneously other various photographic additives are incorporated therein.

The color developing agent used in the present invention is an aromatic primary amine compound. Particularly preferable is a developing agent of p-phenylenediamine type, for example, 4-amino-N,N-diethyl aniline, 3-methyl-4-amino-N,N-diethyl aniline, 4-amino-N-ethyl-N-$\beta$-hydroxyethyl aniline, 3-methyl- 4-amino-N-ethyl-N-β-hydroxyethyl aniline, 3-methyl-4-amino-N-ethyl-N-β-methanesulfonamidoethyl aniline, 3-methyl-4-amino-N-ethyl-N-β-methoxyethyl aniline, 3-β-methanesulfonamidoethyl-4-amino-N,N-diethyl aniline, 3-methoxy-4-amino-N-ethyl-N-β-hydroxyethyl aniline, 3-methoxy-4-amino-N-ethyl-N-β-methoxyethyl aniline, 3-acetamido-4-amino-N,N-diethyl aniline, 4-amino-N-N-dimethyl aniline, N-ethyl-Nβ-[β-(β-methoxyethoxy)ethoxy]ethyl-3-methyl-4-amino aniline, N-ethyl-N-β-(β-methoxyethoxy)ethyl-3-methyl-4-amino aniline, etc. or salts thereof, for example, sulfates, hydrochlorides, sulfites, and p-toluenesulfonates.

Photographic additives used in the above-mentioned color developers include alkali agents (e.g. hydroxides, carbonates and phosphates of alkali metals or ammonium), pH adjusting agents or buffer agents (e.g. weak acids or bases such as acetic acid or boric acid and salts thereof), development accelerators (e.g. pyridinium compounds, cationic compounds, potassium nitrate or sodium nitrate, polyethylene condensates or derivatives thereof, nonionic compounds such as polythioethers, polymer compounds having sulfite esters, pyridine, ethanolamines, benzyl alcohol, hydrazines, etc.), antifoggants (e.g. alkali bromides, alkali iodides, nitrobenzoimidazoles, mercaptobenzoimidazole, 5-methylbenzotriazole, compounds for rapid processing solutions, benzothiazolium derivative of nitrobenzoic acid and phenadine N-oxides), anti-stain or anti-irradiation agents, multi-layer effect accelerators, and stabilizing agents (e.g. sulfites, bisulfites, hydroxylamine hydrochlorides, form sulfite, alkanolamine sulfite addition products, etc.).

The light-sensitive silver halide color photographic materials subjected, after imagewise exposure to light, followed by color development treatment, to ordinary photographic processing. The photographic processing includes, for example, treatment of the developed photographic materials with a stopping solution containing an organic acid, a stop-fixing solution containing fixing components such as an organic acid and hypo or ammonium thiosulfate or the like, a fixing solution containing a fixing component such as hypo or ammonium thiosulfate or the like, a bleaching solution containing ferric salts of aminocarboxylic acids and halogenated alkali as main components, a bleach-fixing solution containing fixing components such as ferric salts of aminopolycarboxylic acids and hypo or ammonium thiosulfate or the like, other processing solutions such as a stabilizing solution, and water-washing and drying, and these processing steps may be suitably selected and employed in combination.

The present invention is concretely illustrated below with reference to examples. However, it should be construed that embodiments of the invention are not limited to these examples only.

EXAMPLE 1

Sample 1 according to the present invention was prepared by the procedure indicated below.

Sample 1

To a mixed liquid comprising 10 ml of dibutyl phthalate and 20 ml of butyl acetate was added 10 g of exemplified coupler (Cp-42), and the mixture was heated to 60° C., so that the coupler was completely dissolved to give a solution of said coupler. This solution was mixed with 5 ml of a 10% aqueous solution of Alkanol B (alkylnaphthalene sulfonate produced and sold by E. I. Du Pont de Nemours & Co.) and 100 ml of a 5% aqueous gelatin solution. The mixture was emulsified by means of a colloid mill to give a dispersion containing the coupler.

The thus prepared coupler dispersion was added to 1 kg of a high sensitive gelatin silver iodobromide emulsion, and the emulsion was coated on a film base and then dried to prepare a light-sensitive silver halide color photographic material which was then designated as sample 1.

Subsequently, comparative samples 2 to 7 were prepared in exactly the same manner as in the case of sample 1, except that the below-mentioned comparative couplers were respectively used in place of the exemplified coupler (Cp-42).

Sample 2

Comparative coupler of the following formula.

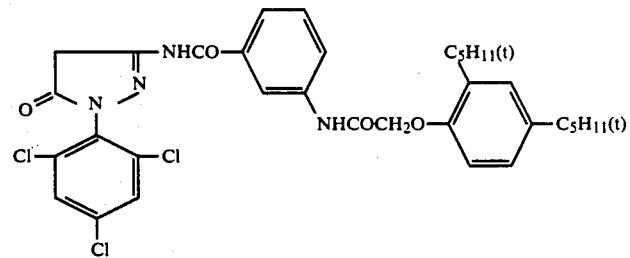

Sample 3

Comparative coupler of the following formula.

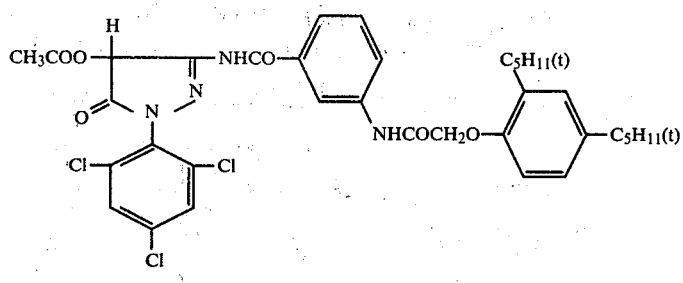
Sample 4
Comparative coupler of the following formula.
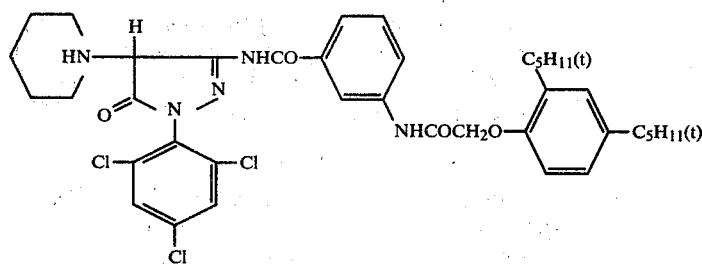
Sample 5
Comparative coupler of the following formula.
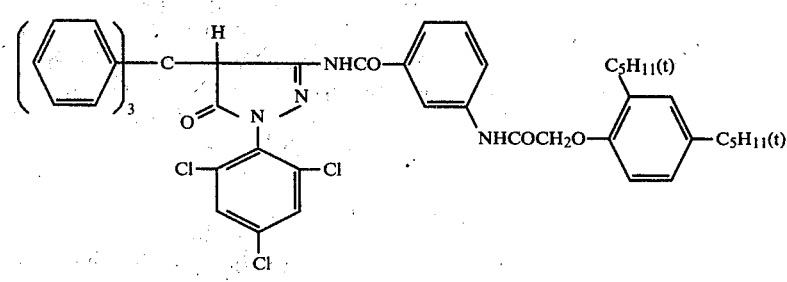
Sample 6
Comparative coupler of the following formula.
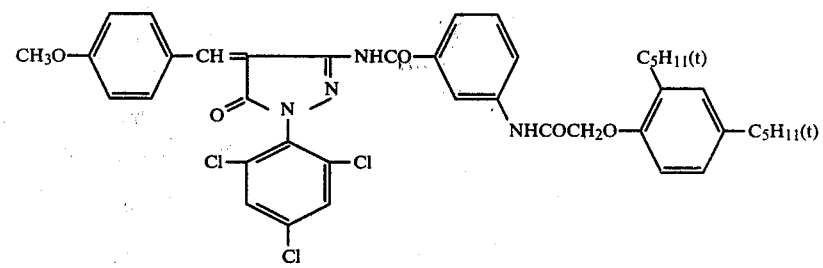
Sample 7
Comparative coupler of the following formula.
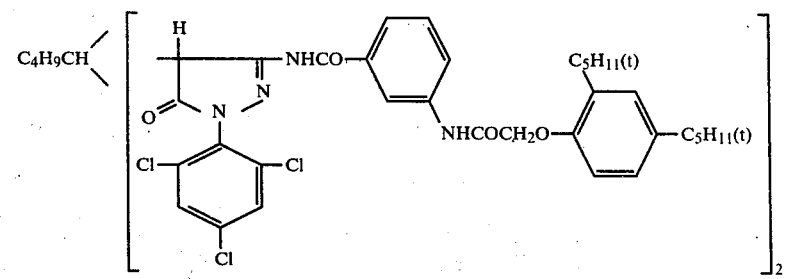

The thus prepared samples were subjected to formalin treatment by retaining them in an atmosphere containing 10 ppm of formalin and those which had not been subjected to the formalin treatment were individually wedgewise exposed to light through a green filter and then subjected to development treatment through the following processing steps.

| Processing step (38° C.) | Processing time |
|---|---|
| Color development | 3 minutes and 15 seconds |
| Bleaching | 6 minutes and 30 seconds |
| Water-washing | 3 minutes and 15 seconds |
| Fixing | 6 minutes and 30 seconds |
| Water-washing | 3 minutes and 15 seconds |
| Stabilization bath | 1 minute and 30 seconds |

The processing solutions individually used in the above-mentioned processing steps had their respective compositions as mentioned below.

Composition of color developer

| | |
|---|---|
| 4-Amino-3-methyl-N-ethyl-N-($\beta$-hydroxyethyl)-aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Nitrilotriacetate trisodium salt (monohydrate) | 2.5 g |
| Potassium hydroxide | 1.0 g |
| Water to make 1 liter and adjust to pH 10.0 with potassium hydroxide. | |

Composition of bleaching solution

| | |
|---|---|
| Iron ammonium salt of ethylenediamine tetraacetate | 100.0 g |
| Diammonium salt of ethylenediamine tetraacetate | 10.0 g |
| Ammonium bromide | 150.0 g |
| Glacial acetic acid | 10.0 ml |
| Water to make 1 liter and adjust to pH 6.0 with ammonia water. | |

Composition of fixing solution

| | |
|---|---|
| Ammonium thiosulfate (50% aqueous solution) | 16.2 ml |
| Anhydrous sodium sulfite | 12.4 g |
| Water to make 1 liter and adjust to pH 6.5 with acetic acid. | |

Composition of stabilizing solution

| | |
|---|---|
| Formalin (37% aqueous solution) | 5.0 ml |
| Konidax (produced and sold by Konishiroku Photo Industry Co., Ltd.) | 7.5 ml |
| Water to make 1 liter. | |

The developed samples which had been subjected to the formalin treatment and those which had not been subjected to said treatment were individually measured in maximum density to obtain the results as shown in the following Table 1.

In Table 1, the residual density (%) was calculated on the basis of the equation, (Density of the formalin treated sample/density of the untreated sample) x 100.

Table 1

| Sample No. | Maximum density (Dmax) Untreated | Maximum density (Dmax) Treated | Residual density (%) |
|---|---|---|---|
| 1 | 2.27 | 2.22 | 98 |
| 2 (Comparative) | 2.34 | 1.24 | 53 |
| 3 (Comparative) | 2.82 | 1.34 | 48 |
| 4 (Comparative) | 2.56 | 1.28 | 50 |
| 5 (Comparative) | 2.49 | 1.15 | 46 |
| 6 (Comparative) | 1.53 | 1.02 | 67 |
| 7 (Comparative) | 2.00 | 1.10 | 55 |

As is clear from Table 1, it is understood that in the case of the sample containing the coupler used in the present invention, the drop in density is found to be very small and thus said coupler is useful.

EXAMPLE 2

High-sensitive multi-layer color negative materials (samples Nos. 8, 9, 10 and 11) each having the following layers formed on a transparent polyethylene terephthalate film support were prepared.

First layer: Antihalation layer, i.e. a gelatin layer containing black colloid silver (dry film thickness 1 $\mu$).

Second layer: Intermediate layer, i.e. a gelatin layer containing 2,5-di-tert-octylhydroquinone (dry film thickness 1 $\mu$).

Third layer: Red-sensitive emulsion layer, i.e. a red-sensitive silver iodobromide emulsion layer (containing 8 mole% of silver bromide and 92 mole% of silver bromide; the amount of silver coated being 3.5 g/m$^2$ and dry film thickness being 6 $\mu$) containing, per mole of silver halide, $6.8 \times 10^{-2}$ mole of 1-hydroxy-N-{$\delta$-(2,4-di-tert-amylphenoxy)-butyl}-2-naphthamide as a cyan coupler, $1.7 \times 10^{-2}$ mole of 1-hydroxy-N-{$\delta$-(2,4-di-tert-amylphenoxy)-butyl]-4-(2-ethoxycarbonylphenylazo)-2-naphthamide as a colored coupler and $4 \times 10^{-3}$ mole of 2-(1-phenyl-5-tetrazolythio)-4-octadecylsuccinimido-1-indanone as a development inhibitor releasing substance (DIR substance).

Fourth layer: Intermediate layer, i.e. the same layer as the second layer.

Fifth layer: Green-sensitive emulsion layer.

Sixth layer: The fifth and sixth layers are individually a green-sensitive silver halide emulsion layer having the composition comprising couplers, etc. in the manner as indicated in the following table. That is, the fifth layer is a first green-sensitive low speed silver iodobromide emulsion layer (containing 8 mole% of silver iodide and 92 mole% of silver bromide; the amount of silver coated being 1 g/m$^2$ and dry film thickness being 3.5 $\mu$), and the sixth layer is a second green-sensitive high speed silver iodobromide emulsion layer (containing 6 mole% of silver iodide and 94 mole% of silver bromide; the amount of silver coated being 1.2 g/m$^2$ and dry film thickness being 2.5 ↑).

| Layer | Couplers, etc. | | Sample 8 | Sample 9 | Sample 10 | Sample 11 |
|---|---|---|---|---|---|---|
| Sixth layer | Coupler | | Exemplified coupler Cp - 17 $1.6 \times 10^{-2}$ | Exemplified coupler Cp - 17 $1.6 \times 10^{-2}$ | Coupler - B (Note 2) $2.9 \times 10^{-2}$ | Coupler - A (Note 1) $5.8 \times 10^{-2}$ |
| | Colored coupler (Note 3) | | $1.7 \times 10^{-2}$ | $1.7 \times 10^{-2}$ | $1.7 \times 10^{-2}$ | $1.7 \times 10^{-2}$ |
| | DIR substance (Note 4) | | — | — | $0.7 \times 10^{-2}$ | — |
| Fifth layer | Coupler | | Exemplified coupler Cp - 17 $0.25 \times 10^{-2}$ | Coupler - A (Note 1) $1.0 \times 10^{-2}$ | Exemplified coupler Cp - 17 $0.25 \times 10^{-2}$ | Coupler - A (Note 1) $1.0 \times 10^{-2}$ |
| | Colored coupler (Note 3) | | $0.5 \times 10^{-2}$ | $0.5 \times 10^{-2}$ | $0.5 \times 10^{-2}$ | $0.5 \times 10^{-2}$ |
| | DIR substance (Note 4) | | $0.2 \times 10^{-2}$ | $0.2 \times 10^{-2}$ | $0.2 \times 10^{-2}$ | $0.2 \times 10^{-2}$ |

(Unit: mole per mole of silver halide)

(Note 1) Coupler - A: 1-(2,4,6-trichlorophenyl)-3-[3-{α-(2,4-di-tert-amylphenoxy)acetamido}benzamido]-5-pyrazolone (Note 2) Coupler - B: 4,4'-Methylene-bis-[1-(2,4,6-trichloro-phenyl)-3-[3-{α-(2,4-di-tert-amylphenoxy)-acetamido}benzamido]-5-pyrazolone (Note 3) Colored coupler: 1-(2,4,6-trichlorophenyl)-3-(2-chloro-5-octadecenylsuccinimidoanilino)-4-(4-hydroxyphenylazo)-5-oxo-2-pyrazolone (Note 4) Development inhibitor releasing type substance (DIR substance): 2-(1-Phenyl-5-tetrazolyl-thio)-4-octadecylsuccinimido-1-indanone Seventh layer: Intermediate layer, i.e. the same layer as the second layer.

Eighth layer: Yellow filter layer, i.e. a gelatin layer containing yellow colloid 2,5-di-tertoctylhydroquinone (dry film thickness 1 μ).

Ninth layer: Blue-sensitive emulsion layer, i.e. a blue-sensitive silver iodobromide emulsion layer (containing 7 mole% of silver iodide and 93 mole% of silver bromide; the amount of silver coated being 1.2 g/m² and dry film thickness being 7 μ) containing, per mole of silver halide, $2.5 \times 10^{-1}$ mole of α-pivaryl-α-(3,5-dioxo-1,2-diphenylimidazolidine-4-yl)-2-chloro-5-{γ-(2,4-di-tert-amylphenoxy)-butylamido}-acetanilide as a yellow coupler and $5 \times 10^{-3}$ mole of ω-bromo-ω-(1-phenyl-5-tetrazolylthio)-4-lauroylamidoacetophenone.

Tenth layer: Protective layer, i.e. a gelatin layer (dry film thickness 1 μ).

The thus prepared samples were individually wedge-exposed to light through a green filter and then subjected to development treatment in the same manner as in Example 1.

Each of the samples thus developed was subjected to sensitometry (using a sensitometer PD-7R manufactured by Konishiroku Photo Industry Co., Ltd.) through green light to determine speed (S), fog (Fog), maximum density (Dmax) and graininess (RMS). Furthermore, each of the said samples was subjected to formalin treatment in the same manner as in Example 1 and then subjected to sensitometry to determine maximum density (Dmax). The graininess (RMS), however, was represented by a value 1000 times the normal deviation of variation in density value when scanned with a microdensitometer of a circular scan caliber of 25 μ. The results obtained were as shown in Table 2.

Table 2

| Sample No. | S | Fog | Dmax Untreated with formalin | Dmax Treated with formalin | Graininess (RMS) |
|---|---|---|---|---|---|
| 8 | 95 | 0.13 | 2.30 | 2.28 | 40 |
| 9 | 100 | 0.16 | 2.35 | 2.30 | 43 |
| 10 | 143 | 0.21 | 2.57 | 2.20 | 45 |
| 11 | 100 | 0.19 | 2.40 | 1.22 | 47 |

As can be seen from Table 2, the samples 8, 9 and 10 each containing the coupler of the present invention, as compared with the sample 11, are found to be quite excellent in graininess, and the drop in density in each of the samples 8, 9 and 10 is found to be very small.

As is clear from the results obtained in the case of the sample 10, there is obtained a light-sensitive silver halide color photographic material excellent in both color forming rate and persistance to formalin gas when the coupler —B which has heretofore been believed to be satisfactory in color forming rate but found to be somewhat poor in persistance to formalin gas is used in combination with the coupler of the present invention.

Accordingly, it is understood that the couplers of the present invention are very useful even when they are used in light-sensitive multi-coated color photographic materials.

Separately, each of the above-mentioned samples as prepared, after having been allowed to stand, as it was, at 25° C. for 3 months, was color-developed to obtain a maximum density value of the magenta color image formed thereon, and each of the samples as prepared was immediately color-developed to obtain a maximum density value of the magenta color image formed thereon. The maximum density value as measured in the former case was divided by that measured in the latter case to obtain the result in terms of percent as shown in the following table.

| Sample No. | 8 | 9 | 10 | 11 |
|---|---|---|---|---|
| Result (%) | 97 | 92 | 89 | 78 |

As is clear from the above table, it is understood that the sample 11 shows a markedly poor color formation, whereas the samples 8, 9 and 10 each containing the coupler of the present invention are found to be stable showing a very slight poor color formation with the lapse of time and thus the couplers used in the present invention are useful. Example 3

On a cellulose triacetate film base having formed thereon an antihalation layer and a gelatin layer was coated thereon a red-sensitive silver halide emulsion layer so that the amount of silver coated became 1.72 g/m$^2$. Into this silver halide emulsion layer, in that case, were incorporated a sensitizing dye for imparting red-sensitivity thereto and, in addition thereto, incorporated common additives such as a hardener, extender, etc. Further, this silver halide emulsion layer was incorporated with, as a cyan coupler, a solution in a mixture of tricresyl phosphate and ethyl acetate of 2-[β-(2,4-di-t-amylphenoxy)butylamido]-4,6-dichloro-5-methyl-phenol so that the amount of the cyan coupler incorporated became $1.3 \times 10^{-1}$ mole per mole of the silver halide and further with Alkanol B (produced and sold by E. I. du Pont de Nemours & Co.), and the silver halide emulsion was emulsified to prepare a coupler dispersion.

Subsequently, a gelatin layer was formed as an intermediate layer on the red-sensitive layer.

On the gelatin layer thus formed was coated a green-sensitive silver halide emulsion layer so that the amount of silver coated became 17 g/m$^2$. In that case, this silver halide emulsion was incorporated with a sensitizing dye for imparting green-sensitivity thereto and further with common additives such as a hardener, extender, etc.

This green-sensitive emulsion layer was further incorporated, in that case, with a solution of exemplified coupler (Cp-33) as a magenta coupler in a mixture of tricresyl phosphate and ethyl acetate so that the amount of the cyan coupler became $1.0 \times 10^{-1}$ mole per mole of the silver halide.

On the green-sensitive emulsion layer was then formed a gelatin layer as an intermediate layer. On the intermediated layer thus formed was further coated a blue-sensitive silver halide emulsion layer so that the amount of silver coated became 4.3 g/m$^2$. In that case, this silver halide emulsion layer was incorporated, in addition to common additives such as a hardener, extender, etc., with a solution of a α-pivaloyl-α-(1-benzyl-2-phenyl-3,5-dioxoimidazolidine-4-il)-2-chloro-5-{γ-(2,4-di-t-amylphenoxy)butylamido}acetanilide as a yellow coupler in a mixture of tricresyl phosphate and ethyl acetate so that the amount of the yellow coupler coated became $2 \times 10^{-1}$ mole per mole of the silver halide and further with Alkanol B.

Subsequently, a gelatin layer as a protective layer was formed on the blue-sensitive emulsion layer.

In the manner above explained, a sample of color reversal film was prepared.

This sample was processed according to the following processing steps using the processing solutions having their respective compositions as mentioned below.

| Processing step | Processing time | Processing temperature |
| --- | --- | --- |
| First development | 3 minutes | 38° C. |
| First stopping | 6 minutes and 30 sec. | " |
| Water-washing | 1 minute | " |
| Color development | 3 minutes 40 sec. | 43° C. |
| Second stopping | 0 minutes 30 sec. | 38° C. |

-continued

| Processing step | Processing time | Processing temperature |
| --- | --- | --- |
| Water-washing | 1 minute | " |
| Bleaching | 6 minutes | " |
| Fixing | 6 minutes | " |
| Water-washing | 3 minutes | " |
| Stabilizing | 0 minutes and 50 sec. | " |

In the above-mentioned processing steps, if necessary, the steps of film hardening and neutralization may be carried out prior to the second development.

| | |
| --- | --- |
| [First developer solution] | |
| Sodium polyphosphate | 2.0 g |
| Sodium bisulfite (anhydrous) | 8.0 g |
| Phenidone | 0.35 g |
| Sodium sulfite | 37.0 g |
| Hydroquinone | 5.5 g |
| Sodium carbonate | 33.0 g |
| Sodium thiocyanate (10% aqueous solution) | 13.8 ml |
| Sodium bromide | 1.3 g |
| Potassium iodide (0.1% aqueous solution) | 13.0 ml |
| Water to make 1 liter    pH= 9.9 ± 0.1 | |
| (Color developer solution) | |
| Sodium polyphosphate | 5.0 g |
| Benzyl alcohol | 4.5 g |
| Sodium sulfite | 7.5 g |
| Trisodium phosphate dodecahydrate | 31.0 g |
| Sodium bromide | 0.9 g |
| Potassium iodide (0.1% aqueous solution) | 90 ml |
| Sodium hydroxide to be added as a pH regulator in a suitable amount, | |
| 4-Amino-N-ethyl-N-(β-methanesulfonamidoethyl)-n-toluidinesesquisulfate monohydrate | 11.0 g |
| Ethyleneamine | 3.0 g |
| 1-Butylaminoborane hydride | 0.07 g |
| Water to make 1 liter    pH 11.5 ± 0.1 | |
| [First and second stopping baths] | |
| Acetic acid | 15 ml |
| Sodium hydroxide | 10.0 g |
| Water to make 1 liter    pH 5.6 ± 0.1 | |
| [Bleaching solution] | |
| EDTA- ferric ammonium salt | 170 g |
| Ammonium bromide | 300 g |
| Water to make 1 liter    pH 5.9 + 0.1 | |
| [Fixing solution] | |
| Sodium thiosulfate (anhydrous) | 94.5 g |
| Sodium bisulfite (anhydrous) | 17.6 g |
| Disodium phosphate | 15.0 g |
| Water to make 1 liter    pH 5.9 ± 0.2 | |
| [Stabilizing bath] | |
| Polyoxyethylene ether alcohol | 0.15 g |
| Formaldehyde (37.5% solution) | 6.0 g |
| Water to make 1 liter. | |

From the sample thus developed, it was understood that the sample shows a favorable colored image and thus the couplers used in the present invention are also useful for the reversal development.

Furthermore, this example was repeated, except that exemplified couplers (Cp-13) and (Cp-20) were individually used in place of the exemplified coupler (Cp-33), to find that the results similar to those of the present example were obtained.

EXAMPLE 4

There was prepared a sample of color print paper having thereon the following constitutive layers.

First layer: A blue-sensitive silver halide emulsion layer (the amount of silver coated: 400 mg/m$^2$) containing an emulsified dispersion of 2-equivalent yellow coupler.

The silver halide emulsion used in this emulsion layer had contained the following main ingredients.

2-Equivalent yellow coupler: α-Pivaloyl-α-(2,4-dioxo-1-benzylimidazolidine-3-il)-2-chloro-5-[γ-(2,4-di-(t)amylphenoxy)butylamido]-acetanilide ($2 \times 10^{-1}$ mole per mole of silver halide)

Silver halide: Silver chloroiodobromide containing 1 mole% of silver iodide and 80 mole% of silver bromide (containing 400 g of gelatin per mole of silver halide).

Sensitizing dye ($2.5 \times 10^{-4}$ mole per mole of silver halide) having the following structure.

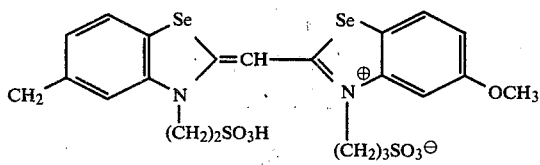

Second layer: A intermediate layer consisting of gelatin (Dry film thickness 1 μ)

Third layer: A green-sensitive silver halide emulsion layer containing an emulsified dispersion shown in Table (a) (The amount of silver coated: 500 mg/m².)

The silver halide emulsion used in the third layer had contain the following main ingredients.

Silver halide: Silver chlorobromide containing 80 mole% of silver bromide (containing 500 g of gelatin per mole of silver halide)

Sensitizing dye ($2.5 \times 10^{-4}$ mole per mole of silver halide) having the following structure.

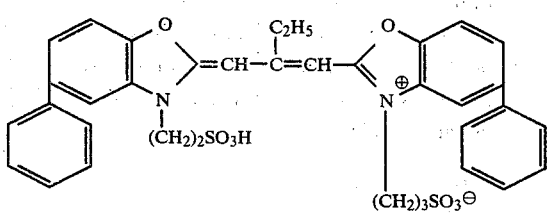

Table (a)

| Composition of emulsified dispersion | Amount |
|---|---|
| Exemplified coupler (Cp - 31) | $1 \times 10^{-1}$ mole per mole of silver halide |
| 2,2,4-Trimethyl-6-hydroxy-7-(t)-octylchroman | $1 \times 10^{-1}$ mole per mole of silver halide |
| Butyl phthalate | 134 ml |
| Ethyl acetate | 268 ml |

Fourth layer: A gelatin layer containing 2,5-di-t-octylhydroquinone (50 mg/m²), 2-(benzotriazole-2-il)-4,6-di-(t)butylphenol (50 mg/m²) and 2-(benzotriazole-2-yl)-4-(t)butylphenol (50 mg/m²) and having a dry film thickness of 2 μ.

Fifth layer: A red-sensitive silver halide emulsion layer (the amount of silver coated: 500 mg/m²) containing an emulsified dispersion of 2-equivalent cyan coupler.

The silver halide emulsion used in the fifth layer had contained the following main ingredients.

2-Equivalent cyan coupler: 2-[α-(2,4-di-(t)amylphenoxy)butylamido]-4,6-dichloro-5-methylphenol ($2 \times 10^{-1}$ mole per mole of silver halide).

Sensitizing dye ($2.5 \times 10^{-4}$ mole per mole of silver halide) having the following structure.

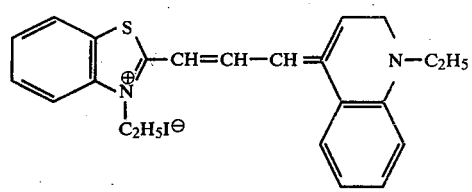

Silver halide: Silver chlorobromide containing 80 mole% of silver bromide (containing 500 g of gelatin per mole of silver halide).

Sixth layer: A protective layer consisting of gelatin (dry film thickness 1 μ).

The silver halide emulsions respectively used in forming the first, third and fifth layers of the sample were individually prepared according to the procedure disclosed in Japanese Patent Publication No. 7772/1971. Each of said emulsions was subjected to chemical sensitization using sodium thiosulfate pentahydrate and incorporated with 4-hydroxy-6-methyl-1,3,3a,7-tetrazaindene sodium salt as a stabilizer and bis(vinylsulfonylmethyl)-ether as a hardener and further with saponin as a coating aid.

The color pint paper thus prepared was wedgewise exposed to light through each of blue and red filters and then subjected to each of the following processing to obtain thereon yellow, magenta and cyan color images.

| Color development processing (31° C.) | Processing time |
|---|---|
| Color development | 3 minutes |
| Bleach-fixing | 1 minute |
| Water-washing | 2 minutes |
| Stabilization | 1 minute |
| Water-washing | 10 minutes |

Drying (below 95° C.)

The processing solutions individually used in the above-mentioned processing steps were as follows:

Composition of color developer:

| | |
|---|---|
| N-Ethyl-N-β-methanesulfonamidoethyl-3-methyl-4-aminoaniline sulfate | 4.0 g |
| Hydroxylamine | 2.0 g |
| Potassium carbonate | 25.0 g |
| Sodium chloride | 0.1 g |
| Sodium bromide | 0.2 g |
| Anhydrous sodium sulfite | 2.0 g |
| Benzyl alcohol | 10.0 ml |
| Polyethylene glycol (average polymerization degree: 400) | 3.0 ml |
| Water to make 1 liter and adjust to pH 10.0 with sodium hydroxide. | |

Composition of bleach-fixing solution:

| | |
|---|---|
| Iron sodium salt of ethylenediaminetetraacetic acid | 60.0 g |
| Ammonium thiosulfate | 100.0 g |
| Sodium bisulfite | 10.0 g |
| Sodium metabisulfite | 3.0 g |

-continued

| | |
|---|---|
| Water to make 1 liter and adjust to pH 6.6 with ammonia water. | |

Composition of stabilizing solution:

| | |
|---|---|
| Succinic acid | 10.0 g |
| Formalin (37% aqueous solution) | 15.0 ml |
| Water to make 800 ml and adjust to pH 3.9 with sodium acetate and then water to make 1 liter. | |

Separately, the sample as prepared in the manner explained above was stored in an unexposed state under normal conditions (at 25° C. and 60% RH) for about 3 months and thereafter exposed to light in the same manner as above, followed by development processing in the same way as above.

As the result, there were obtained color prints with favorable color forming properties similar to those of the sample of Example 3.

What we claim is:

1. In a process for forming a magenta dye image comprising imagewise exposing a light-sensitive silver halide photographic material and processing the photographic material in the presence of a magenta coupler and a color developing agent, the improvement wherein the magenta coupler is a compound obtained by reacting at least one 5-pyrazolone compound with a compound having two or more aldehyde groups, said magenta coupler having at least four residues of the 5-pyrazolone compound, from each of which one hydrogen atom at the 4-position has been removed, wherein the compound having aldehyde groups is a compound represented by the following formula:

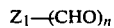

wherein n represents an integer of 2 or more, and when n is 2, $Z_1$ represents a single bond or an aliphatic hydrocarbon residue, aromatic hydrocarbon residue or heterocyclic residue, each of which being divalent, said heterocyclic residue selected from the group consisting of 2,4-furandiyl, 2,5-furandiyl, 2,5-thiophenediyl and 3,5-pyridinediyl, and when n is an integer of 3 or more, $Z_1$ represents an aliphatic hydrocarbon residue, aromatic hydrocarbon residue or heterocyclic residue, each of which being n-valent, said heterocyclic residue being 3,5,7-benzofuranetriyl.

2. A process for forming a magenta dye image according to claim 1 wherein the magenta coupler is a compound represented by the following formula:

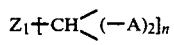

wherein A represents a residue of the 5-pyrazolone compound from which one hydrogen atom at the 4-position has been removed, and n represents an integer of 2 or more, and when n is 2, $Z_1$ is as defined in claim 1, and when n is an integer of 3 or more, $Z_1$ is as defined in claim 1.

3. A process for forming a magenta dye image according to claim 2 wherein the 5-pyrazole compound is a compound selected from the compounds represented by the following formula:

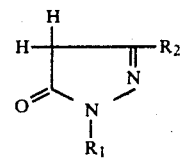

wherein $R_1$ represents a hydrogen atom, an alkyl, alkenyl, cycloalkyl, aryl or heterocyclic group, and $R_2$ represents a hydrogen atom, an alkyl, aryl, heterocyclic, ester, alkoxy, aryloxy, heterocyclo selected from the group consisting of pyridyl, quinolyl, furyl, benzothiazolyl, oxazolyl, imidazolyl, and naphthoxazolyl, alkylthio, arylthio, carboxy, amino, acylamino, ureido, thioureido, carbamoyl, thiocarbamoyl, guanidino or sulfamoyl group.

4. A process for forming a magenta dye image according to claim 1 wherein the 5-pyrazolone compound is a compound selected from the group consisting of 3-acylamino-5-pyrazolone, 3-anilino-5-pyrazolone and 3-ureido-5-pyrazolone and the compound having aldehyde groups is a compound represented by the following general formula:

$$OCH—Z_2—CHO$$

wherein $Z_2$ represnts a single bond, an alkylene, alkenylene, alkynylene, cycloalkylene, arylene or divalent heterocyclic group, said heterocyclic group selected from the group consisting of 2,4-furanediyl, 2,5-furanediyl, 2,5-thiophenediyl and 3,5-pyridinediyl.

5. A process for forming an magenta dye image according to claim 1 wherein the magenta coupler is present in the light-sensitive silver halide photographic material.

6. A process for forming a magenta dye image according to claim 5 wherein the magenta coupler is at least one compound selected from the group consisting of α, α, α', α'-tetrakis(3-acylamino-5-pyrazolone-4-yl)xylene, α, α, α', α'-tetrakis(3-anilino-5-pyrazolone-4-yl)xylene and α, α, α', α'-tetrakis(3-ureido-5-pyrazolone-4-yl)xylene.

7. A process forming a magenta dye image according to claim 5 wherein the magenta coupler is a compound represented by the following general formula:

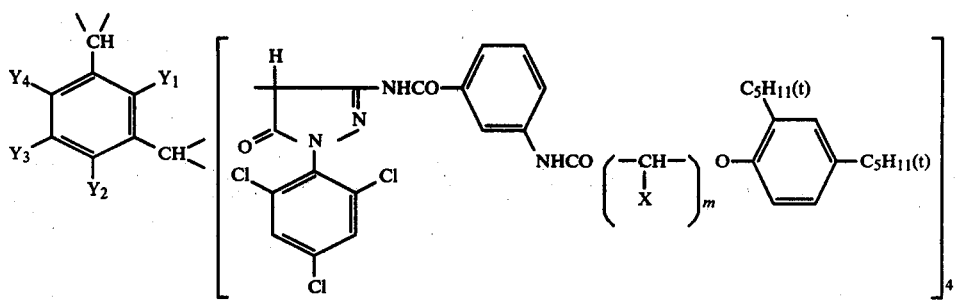

wherein X represents a hydrogen atom or an alkyl group, $Y_1$, $Y_2$, $Y_3$ and $Y_4$ individually represent a hydrogen, a halogen atom, a hydroxy, nitro, cyano, amino, alkyl or alkoxy group and m is an integer of from 1 to 4.

8. A process for forming a magenta dye image comprising imagewise exposure of a light-sensitive silver halide photographic material in the presence of a magenta coupler and a color developing agent wherein the magenta coupler is a compound represented by the formula

wherein A represents a residue of the 5-pyrazolone compound from which one hydrogen atom at the 4-position has been removed, and n represents an integer of 2 or more, and when n is 2, $Z_1$ represents a single bond or an aliphatic hydrocarbon residue, aromatic hydrocarbon residue or heterocyclic residue, each of which being divalent, said heterocyclic residue selected from the group consisting of 2,4-furandiyl, 2,5-furandiyl, 2,5-thiophenediyl and 3,5-pyridinediyl and when n is an integer of 3 or more, $Z_1$ represents an aliphatic hydrocarbon residue, aromatic hydrocarbon residue or heterocyclic residue, each of which being n-valent, said heterocyclic residue being 3,5,7-benzofuranetriyl.

9. A process according to claim 8 wherein the 5-pyrazolone compound is a compound selected from the compounds represented by the following formula:

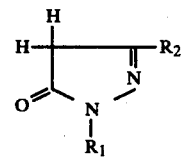

wherein $R_1$ represents a hydrogen atom, an alkyl, alkenyl, cycloalkyl, aryl or heterocyclic group, and $R_2$ represents a hydrogen atom, an alkyl, aryl, heterocyclic, ester, alkoxy, aryloxy, heterocyclo selected from the group consisting of pyridyl, quinolyl, furyl, benzothiazolyl, oxazolyl, imidazolyl, and naphthoxazolyl, alkylthio, arylthio, carboxy, amino, acylamino, ureido, thioureido, carbamoyl, thiocarbamoyl, guanidino or sulfamoyl group.

10. A compound according to claim 8 wherein the magenta coupler is at least one compound selected from the group consisting of $\alpha$, $\alpha$, $\alpha'$, $\alpha'$-tetrakis(3-acylamino-5-pyrazolone-4-yl)-xylene, $\alpha$, $\alpha$, $\alpha'$, $\alpha'$-tetrakis(3-anilino-5-pyrazolone-4-yl)xylene and $\alpha$, $\alpha$, $\alpha'$, $\alpha'$-tetrakis(3-ureido-5-pyrazolone-4-yl)xylene.

11. A process according to claim 8 wherein the magenta coupler is a compound represented by the following formula:

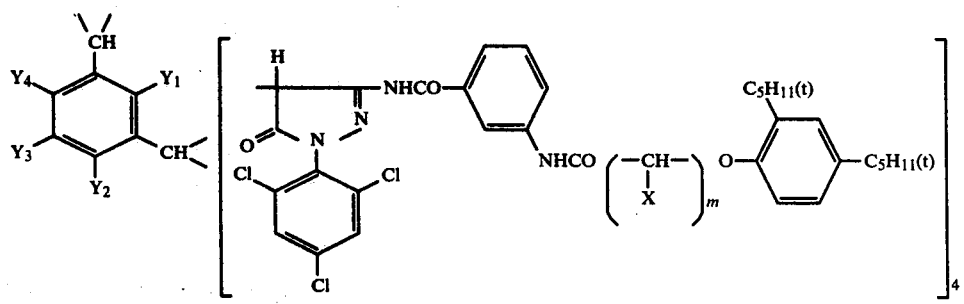

wherein X represents a hydrogen atom or an alkyl group, $Y_1$, $Y_2$, $Y_3$ and $Y_4$ individually represent a hydrogen, a halogen atom, a hydroxy, nitro, cyano, amino, alkyl or alkoxy group and m is an integer of from 1 to 4.

* * * * *